United States Patent [19]

Miyazawa et al.

[11] Patent Number: 5,534,187
[45] Date of Patent: Jul. 9, 1996

[54] LIQUID CRYSTALLINE COMPOUND AND LIQUID CRYSTAL COMPOSITION

[75] Inventors: Kazutoshi Miyazawa; Shuichi Matsui; Yasuyuki Goto; Etsuo Nakagawa; Shinichi Sawada, all of Chiba, Japan

[73] Assignee: Chisso Corporation, Osaka, Japan

[21] Appl. No.: 410,297

[22] Filed: Mar. 24, 1995

[30] Foreign Application Priority Data

Mar. 29, 1994 [JP] Japan .................................. 6-058705

[51] Int. Cl.$^6$ .................. C09K 19/52; G02F 1/13; C07C 25/13
[52] U.S. Cl. .................. 252/299.01; 252/299.61; 252/299.63; 252/299.64; 252/299.65; 252/299.66; 252/299.67; 359/103; 570/127
[58] Field of Search .................. 252/299.01, 299.61, 252/299.63, 299.64, 299.65, 299.66, 299.67; 570/127; 359/103

[56] References Cited

U.S. PATENT DOCUMENTS

| | | | |
|---|---|---|---|
| 4,505,837 | 3/1985 | Römer et al. | 252/299.6 |
| 5,209,868 | 5/1993 | Reiffenrath et al. | 252/299.63 |
| 5,324,449 | 6/1994 | Kurmeier et al. | 252/299.01 |
| 5,342,546 | 8/1994 | Sato et al. | 252/299.6 |
| 5,389,295 | 2/1995 | Wächtler et al. | 252/299.63 |

*Primary Examiner*—Shean C. Wu
*Attorney, Agent, or Firm*—Wenderoth, Lind & Ponack

[57] ABSTRACT

A liquid crystalline compound expressed by the formula

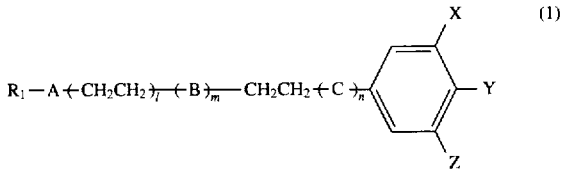

wherein $R_1$ represents an alkyl group of 1 to 12 carbon atoms, and one or two not adjacent $CH_2$ group excluding the terminal in this group may be replaced by —CO— group, —OCO— group, —COO— group or —CH=CH group; X and Z each represents H, F or Cl; Y represents perfluoroalkyl group or perfluoroalkyloxy group of 1 to 4 carbon atoms, and one or two F atoms in this group may be replaced by H; one of A, B and C represents cyclohexene ring and the others thereof are chosen from among covalent bond or cyclohexane group and benzene ring and these rings may be substituted by F or Cl; and l, m and n each are 0 or 1, independently of each other, but when m=0, then l=0. It is possible to provide a liquid crystal composition having a large Δn, a low viscosity and a high voltage-holding ratio, and exhibiting a nematic liquid crystal phase within a broad temperature range and having a very high Δε and a low driving voltage, and preferably used for TFT. Further it is possible to provide a novel liquid crystalline compound preferred as a component for the liquid crystal composition.

10 Claims, No Drawings

LIQUID CRYSTALLINE COMPOUND AND LIQUID CRYSTAL COMPOSITION

BACKGROUND OF THE INVENTION

1. Field of the Invention

This invention relates to a novel liquid crystalline compound and a liquid crystal composition containing the same preferred for TFT.

2. Description of the Related Art

Nematic liquid crystal compositions have been broadly used as display materials for various display use applications such as watch, electronic calculator, word processor, computer terminal, television, etc. The modes for driving liquid crystal display elements using nematic liquid crystal compositions include mainly three kinds of twisted nematic mode (hereinafter abbreviated to TN), super-twisted nematic mode (hereinafter abbreviated to STN) and thin film transistor mode (hereinafter abbreviated to TFT). Among these, TFT mode is superior in the display capability, has been used for television or large type color display and enlargement of its use applications has been most expected.

As the characteristics required for liquid crystalline compounds for TFT, (1) exhibition of nematic liquid crystal phase within a broad temperature range, (2) a large dielectric anisotropy value (hereinafter abbreviated to $\Delta\epsilon$), (3) a large birefringence index (hereinafter abbreviated to $\Delta n$), (4) a low viscosity and (5) a chemical stability and a high voltage-holding ratio are mentioned. In order to satisfy these various characteristics, various compounds have been proposed.

As compounds having a high voltage-holding ratio, compounds containing fluorine atom are superior, and such liquid crystalline compounds have so far been vigorously searched. For example, a compound having 3,4-difluorobenzene core at the terminal of the molecule (DE 3042391) and further a compound having 3,4,5-trifluorobenzene core, aiming at a large $\Delta\epsilon$ (U.S. Pat. No. 5,032,313) have been known, but these compounds have a very low clearing point; hence they are unsuitable.

Further, compounds having trifluoromethyl group, trifluoromethyloxy group or difluoromethyloxy group introduced at the terminal of the molecule (DE 4027840) have also been known, but they have had drawbacks of low clearing point and further a small $\Delta n$.

Further, in recent years, a compound having 1,1,2,2-tetrafluoroethyloxy group at the terminal of the molecule (DE 4142519) and a compound having 2,2,2-trifluoroethyloxy group at the terminal thereof (WO93/3113) have been reported, but either of these compounds have had drawbacks of a low clearing point and no sufficiently large $\Delta\epsilon$ and $\Delta n$; hence they are insufficient in the characteristics. An example of a compound having introduced a cyano group having a larger dipole moment, aiming at exhibition of a larger $\Delta\epsilon$ has been reported (Japanese patent application laid-open Nos. Sho 62-103057 and Sho 63-216858), but in these cases, the viscosity increases and the voltage-holding ratio lowers; hence it has been impossible to use them as liquid crystalline compounds for TFT.

Any of the above compounds disclosed in the prior art contain only a benzene ring and/or a cyclohexane ring, and there are almost no compounds containing a cyclohexene ring. The reason is considered as consisting in that compounds having a cyclohexene ring are liable to cause polymerization, decomposition, etc. due to various environment factors (moisture, heat, air, light, electricity, etc.) and hence are unstable (for example, U.S. Pat. No. 4,405,488).

As only a compound having a stable cyclohexene ring, there is a compound disclosed in Japanese patent application No. Hei 2-90190 (U.S. Pat. No. 5,064,565), but it does not exhibit a sufficiently large $\Delta\epsilon$; hence it has been unsuitable as a liquid crystal compound for TFT.

Further, EP 334911 claims a compound expressed by the formula containing a cyclohexene ring, but as to its concrete compound, there is no description suggesting an example or characteristics supporting it.

Problem to be Solved by the Present Invention

The object of the present invention is to provide a liquid crystalline compound which has overcome the above drawbacks of the prior art, exhibit a nematic liquid crystal phase within a broad temperature range and also has a large $\Delta\epsilon$ and $\Delta n$ and further has a high voltage-holding ratio, and a liquid crystal composition containing the same preferred for TFT.

Means for Solving the Problem

In order to achieve the above object, the inventions to be claimed are as follows:

(1) A liquid crystalline compound expressed by the formula (I)

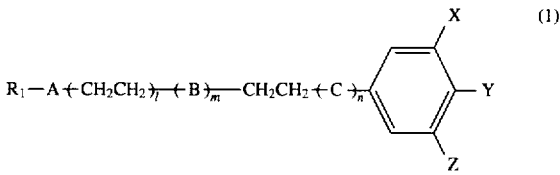

wherein $R_1$ represents an alkyl group of 1 to 12 carbon atoms and one or two not adjacent $CH_2$ groups excluding the terminal in the alkyl group may be replaced by oxygen atom, —CO— group, —OCO— group, —COO— group or —CH=CH— group; X and Z each represent H, F or Cl atom; Y represents a perfluoroalkyl group or a perfluoroalkyloxy group of 1 to 4 carbon atoms and one or two F atoms in these groups may be replaced by H atom; one of A, B and C each represent cyclohexene ring and the others thereof can be chosen from among covalent bond or cyclohexane ring and benzene rings and these rings may be substituted by F atom or Cl atom; and l, m and n each are 0 or 1 independently of each other, but when m=0, l=0.

(2) A liquid crystalline compound according to item (1), wherein $R_1$ represents an alkyl group or an alkyloxy group of 1 to 12 carbon atoms.

(3) A liquid crystalline compound according to item (1), wherein Y represents trifluoromethyl group.

(4) A liquid crystalline compound according to item (1), wherein Y represents trifluoromethyloxy group.

(5) A liquid crystalline compound according to item (1), wherein Y represents difluoromethyloxy group.

(6) A liquid crystalline compound according to item (1), wherein Y represents 1,1,2,2-tetrafluoroethyloxy group.

(7) A liquid crystalline compound according to item (1), wherein Y represents 1,1,2,3,3,3-hexafluoropropyloxy group.

(8) A liquid crystalline compound according to item (1), wherein Y represents pentafluoroethyloxy group.

(9) A liquid crystal composition comprising two or more components at least one of which is a liquid crystalline compound set forth in either one of items (1) to (8).

(10) A liquid crystal composition comprising as a first component, at least one compound set forth in either one of items (1) to (8) and as a second component, at least one compound chosen from among those of the following formulas (2), (3) and (4):

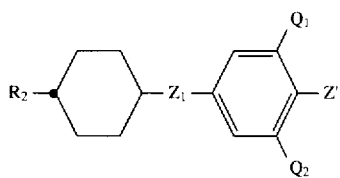
(2)

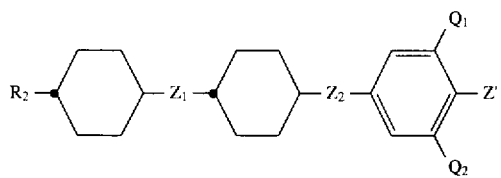
(3)

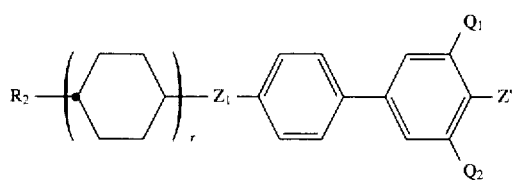
(4)

wherein $R_2$ represents an alkyl group of 1 to 10 carbon atoms; $Z'$ represents F or Cl; $Q_1$ and $Q_2$ each represent H or F independently of each other; r represents 1 or 2; and $Z_1$ and $Z_2$ each represent —$CH_2CH_2$— or covalent bond independently of each other.

(11) A liquid crystal composition comprising as a first component, at least one compound set forth in either one of items (1) to (8), and as a second component, at least one compound chosen from among those of the following formulas (5), (6), (7), (8) and (9):

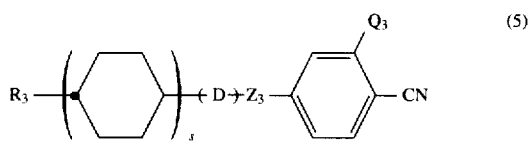
(5)

wherein $R_3$ represents an alkyl group of 1 to 10 carbon atoms or an alkenyl group of 2 to 10 carbon atoms and optional methylene group (—$CH_2$—) excluding the terminal in these groups may be replaced by oxygen atom (—O—), but two or more methylene groups should not be continuedly replaced by oxygen atom; $Z_3$ represents —$CH_2CH_2$—, —COO— or covalent bond; $Q_3$ represents H or F; D represents cyclohexane ring, benzene ring or 1,3-dioxane ring; and s represents 0 or 1,

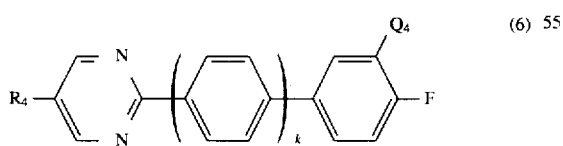
(6)

wherein $R_4$ represents an alkyl group of 1 to 10 carbon atoms, and optional methylene group (—$CH_2$—) excluding the terminal in the group may be replaced by oxygen atom (—O—), but two or more methylene groups should not be continuedly replaced by oxygen atom; $Q_4$ represents H or F; and k represents 0 or 1,

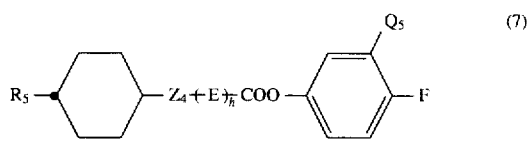
(7)

wherein $R_5$ represents an alkyl group of 1 to 10 carbon atoms, and optional methylene group (—$CH_2$—) excluding the terminal in the group may be replaced by oxygen atom (—O—), but two or more methylene groups should not be continuedly replaced by oxygen atom; E represents cyclohexane ring or benzene ring; $Q_5$ represents H or F; $Z_4$ represents —COO— or covalent bond; and h represents 0 or 1,

(8)

wherein $R_6$ and $R_7$ each represent an alkyl group, an alkyloxy group or an alkyloxymethyl group of 1 to 10 carbon atoms, independently of each other, and optional methylene groups (—$CH_2$—) excluding the terminal in these groups may be replaced by oxygen atom, but two or more methylene groups should not be continuedly replaced by two or more oxygen atoms; L represents cyclohexane ring, pyrimidine ring or benzene ring; G represents cyclohexane ring or benzene ring; and $Z_5$ represents —C≡C—, —COO—, —$CH_2CH_2$— or covalent bond,

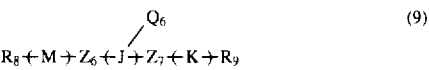
(9)

wherein $R_8$ represents an alkyl group or an alkyloxy group of 1 to 10 carbon atoms; $R_9$ represents an alkyl group, an alkyloxy group or an alkyloxymethyl group of 1 to 10 carbon atoms, and optional methylene group (—$CH_2$—) excluding the terminal in these groups may be replaced by oxygen atom (—O—), but two or more methylene groups should not be continuedly replaced by oxygen atom; M represents cyclohexane ring or pyrimidine ring; J and K each represent cyclohexane ring or benzene ring independently of each other; $Z_6$ represents —COO—, —$CH_2CH_2$— or covalent bond; $Z_7$ represents —C≡C—, —COO— or covalent bond; and $Q_6$ represents H or F.

(12) A liquid crystal display element composed using a liquid crystal composition comprising two or more components, at least one of which contains at least one liquid crystalline compound recited in either one of items (1) to (8).

(13) A liquid crystal display element composed using a liquid crystal composition comprising two or more components, at least one of which contains at least one liquid crystalline compound recited in either one of items (9) to (11).

Any of the liquid crystalline compounds expressed by the formula (I) have superior liquid crystal characteristics, and liquid crystalline compounds having particularly superior characteristics among the above, that is, those which exhibit nematic liquid crystal phase within a broad temperature range, have a large Δε and Δn and a low viscosity and have a high voltage-holding ratio are (1—1) to (1-25) mentioned below:

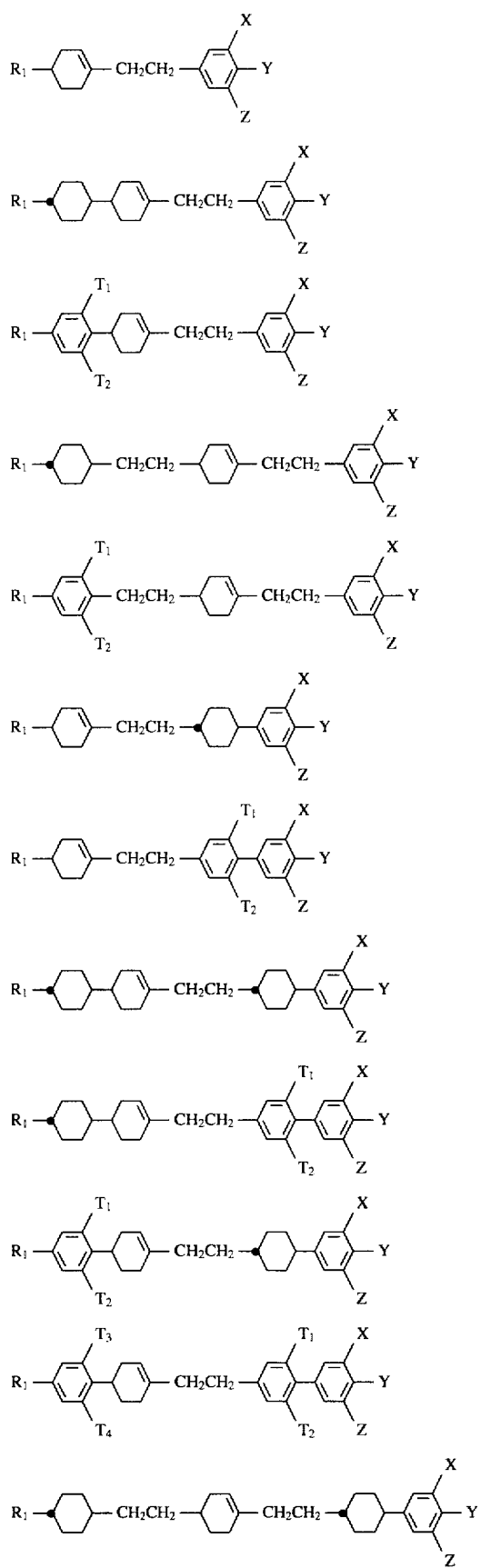

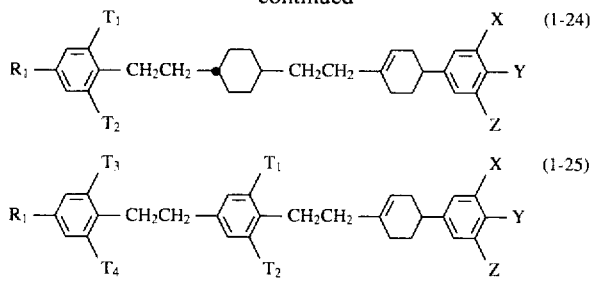

In these formulas, $R_1$, X, Y and Z each are as defined above, and $T_1$, $T_2$, $T_3$ and $T_4$ each represent F or Cl atom independently of each other.

Among the above, those wherein the substituent Y is chosen from among the followings exhibit particularly preferable characteristics:

—$CF_3$  —$OCF_3$
—$CF_2H$  —$OCF_2H$
$CF_2CF_2H$  —$OCF_2CF_2H$
$CF_2CF_3$  —$OCF_2CF_3$
$CF_2CFHCF_3$  —$OCF_2CFHCF_3$

Although any of the compounds expressed by the formula (I) of the present invention can be a component constituting liquid crystal compositions having superior characteristics, tricyclic compounds or tetracyclic compounds are preferably chosen and used in the case where a liquid crystal composition having a particularly high clearing point is required, whereas bicyclic compounds are preferably chosen and used in the case where a liquid crystal composition having a somewhat low clearing point is required. Although any of the compounds of the present invention expressed by the formula (1) exhibit a large Δε, at least one of X, Z, $T_1$, $T_2$, $T_3$ and $T_4$ is preferred to be F or Cl atom, in the case where a particularly large Δε is required, and a compound containing a number of benzene rings is preferred in the case where a large Δn is required. The compounds of the present invention do not contain any cyano group or the like as substituent example raising the viscosity; hence any of them have a low viscosity, but in the case where a lower viscosity is required, a compound containing a number of cyclohexane rings is preferred. As described above, according to the present invention, when X, Z, $T_1$, $T_2$, $T_3$ and $T_4$ as well as the ring core are suitably chosen, it is possible to optionally obtain compounds having necessary values of physical properties.

The compounds of the present invention are prepared by subjecting an alcohol substance obtained by reacting various Grignard reagents with cyclohexanone derivatives, to dehydration reaction.

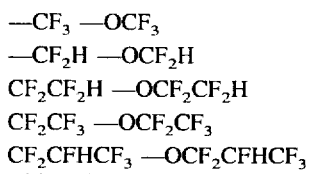

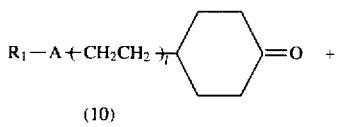

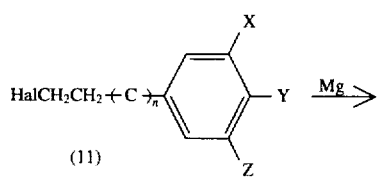

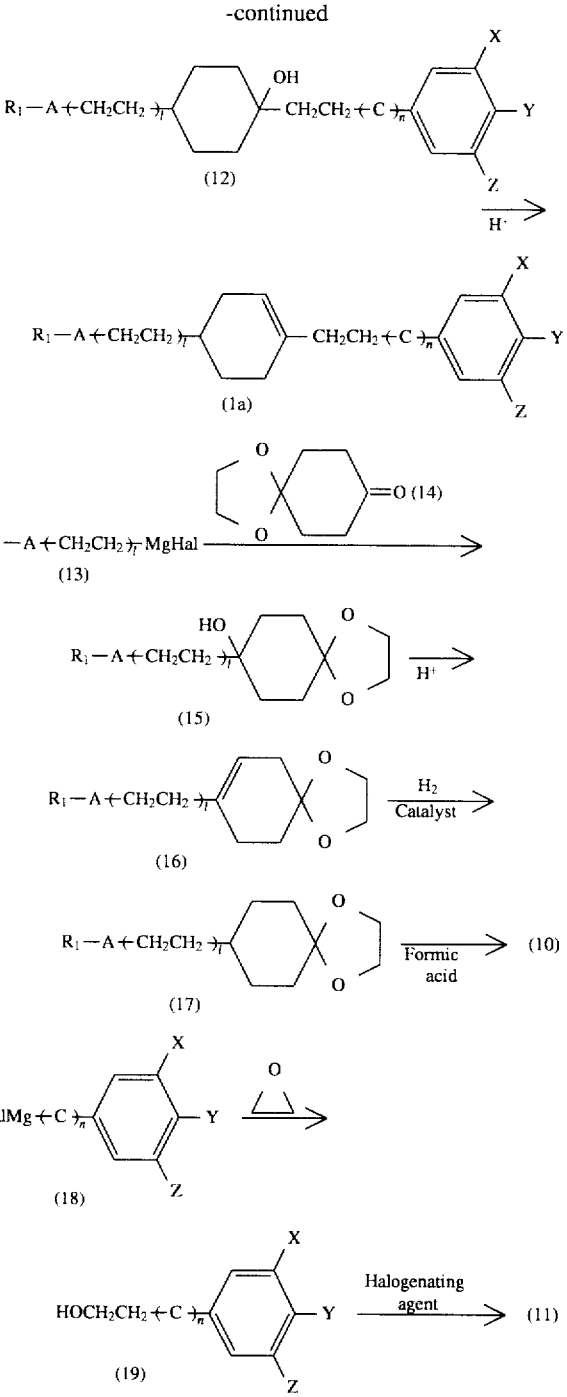

(In the above equations, Hal represents Cl, Br or I and $R_1$, l, n, X, Y, Z, A and C are as defined above.)

Namely, a compound (1a) of the formula (1) wherein B represents a cyclohexene ring can be prepared by reacting a Grignard reagent prepared from a 2—substituted ethyl halide (11), with a cyclohexanone derivative (10) to obtain an alcohol substance (12), followed by dehydrating it. In addition, in the preparation of the above (12) the Grignard reagent may be replaced by a 2-substituted ethyllithium. The above dehydration reaction easily proceeds in the presence of an acidic catalyst. As the acidic catalyst used, mineral acids such as sulfuric acid, hydrochloric acid, etc., sulfonic acids such as p-toluenesulfonic acid or their salts, and acidic ion exchange resins such as Amberlyst, etc. are broadly suitable. Further, compound (1a) can be prepared without isolating (12), by once converting the tertiary hydroxyl group of (12) into a leaving groups such as mesyl group, tosyl group, halogens, etc., followed by treatment with bases such as NaOH, NaH, DBU, etc., or by reacting a Grignard reagent prepared from (11), with (10), followed by bringing the reaction system into an acidic condition.

The starting raw material (10) can be obtained by reacting compound (13) with commercially available 1,4-cyclohexanedione monoethylene ketal (14) to obtain (15), followed by subjecting it to dehydration, reduction, and removal of protective group. The dehydration reaction can be carried out in the same manner as the above. Further, the reduction reaction can be carried out in a hydrogen atmosphere in the presence of a catalyst such as Pd-C, Pt-C, Raney Ni, etc. Further, the reaction of removal of protective group can be easily carried out by heating (17) under an acidic condition, preferably in formic acid. (11) used for preparing the Grignard reagent is prepared by halogenating an alcoholic substance (19) obtained by subjecting compound (18) to carbon-number-increasing reaction, with various halogenating agents. As the halogenating agents, hydrogen bromide, hydrobromic acid, phosphorus tribromide, thionyl chloride, etc. are preferably mentioned. The carbon number-increasing reaction may be carried out according to a known process of effecting the reaction, but a process of using ethylene oxide is most simple and preferable.

Next, compound (1b) of the formula (1) wherein C represents cyclohexene ring can be prepared by reacting a Grignard reagent prepared from 2-substituted ethylhalide (20), with cyclohexanone derivative (21), to obtain an alcoholic substance (22), followed by dehydrating it.

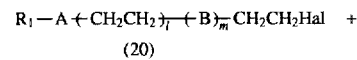

(20)

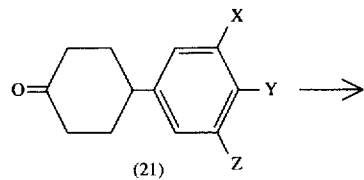

(21)

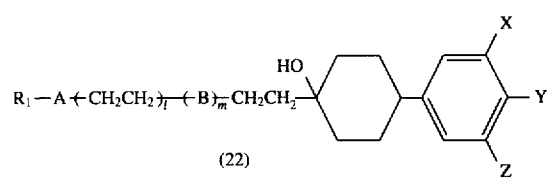

(22)

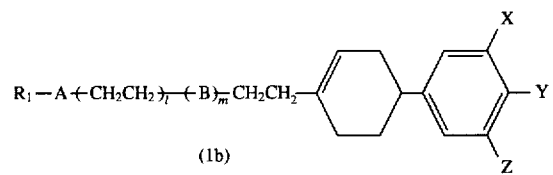

(1b)

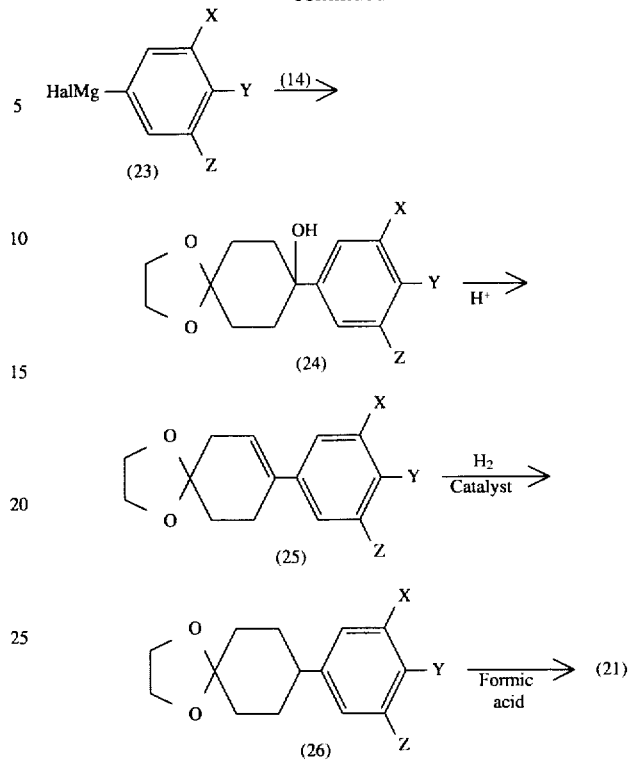

(In the above equations, $R_1$, l, m, X, Y, Z, A, B and Hal are as defined above.)

In addition, in the preparation of the above (22), the Grignard reagent can be replaced by 2-substituted ethyllithium. The above dehydration reaction may be carried out as above. The starting raw material (21) can be obtained by reacting commercially available 1,4-cyclohexanedione monoethylene ketal (14) with a phenylmagnesium halide (23) to obtain (24), followed by subjecting it to dehydration, reduction and protective group-removing reaction as in the case of preparation of the above (10).

In addition, in any of the above preparation processes, if the Y in the formula contains hydrogen atom, the reactivity of this hydrogen is very high; hence these preparation processes cannot be applied. Thus, in such a case, the following process is suitable:

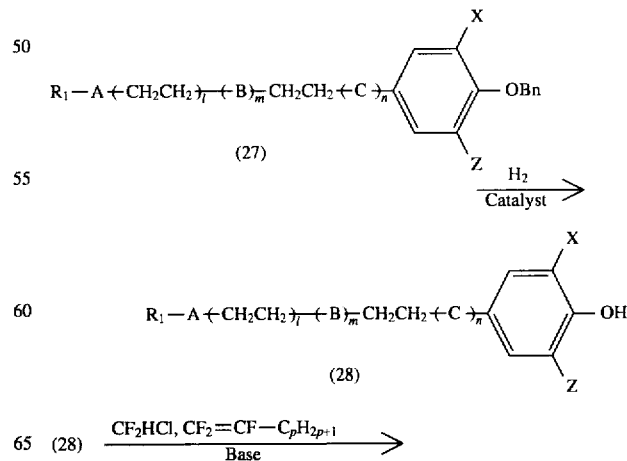

(28) $\xrightarrow[\text{Base}]{CF_2HCl, CF_2=CF-C_pH_{2p+1}}$

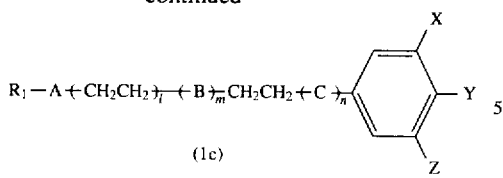

(1c)

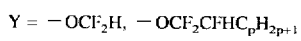

(In the above equations, Bn represents benzyl group; p represents an integer of 0 to 2; and $R_1$, l, m, n, X, Z, A, B and C are as defined above.)

Namely, a compound (27) wherein Y represents benzyl ether is obtained in advance, followed by removing the benzyl ether to obtain a compound (28) having a hydroxyl group, and introducing a fluoroalkyl group into the phenolic hydroxyl group, to obtain a compound of the formula (1c). In this case, it does not matter if a protective group other than benzyl ether, for example, silyl ethers such as trimethylsilyl ether, acetals such as methoxymethyl ether is used, etc. is used. Introduction of a fluoroalkyl group into (28) can be carried out by reacting various fluorine-containing compounds under basic condition.

Any of the thus obtained compounds (1) of the present invention exhibit a large $\Delta\epsilon$ and $\Delta n$, and are chemically stable in spite of containing cyclohexene ring; hence they have a high voltage-holding ratio and further are easily miscible with various liquid crystal compounds; thus they are far superior as a component of nematic liquid crystal compositions, particularly of nematic liquid crystal compositions suitable to electro-optical elements.

The liquid crystal composition provided by the present invention may be composed only of component (A) containing at least one compound expressed by the formula (1), but a mixture of the above component (A), with as a second component, at least one compound chosen from the groups consisting of the above formulas (2), (3) and (4), and/or at least one compound chosen from the groups consisting of the above formulas (5), (6), (7), (8) and (9) is preferable, and further, in accordance with the objects, compounds optionally chosen from compounds of the groups (B) having $\Delta\epsilon \geq 5$, those of the group (C) having $|\Delta\epsilon|<5$, those of the group (D) having a clearing point of particularly 80° C. or higher, and those of the group (E) other than the above, can be mixed.

Among the above second components, as preferable examples of compounds included in the formula (2), the following (2-1) to (2-12) can be mentioned:

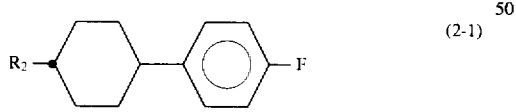

(2-1)

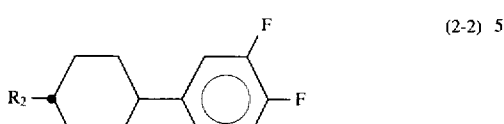

(2-2)

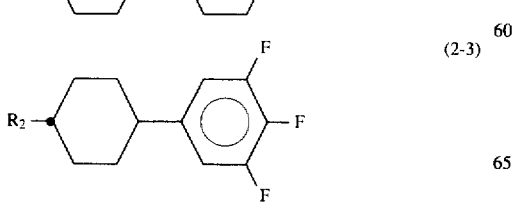

(2-3)

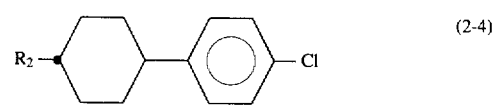

(2-4)

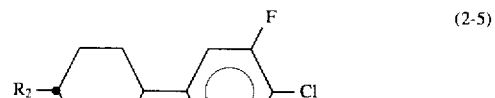

(2-5)

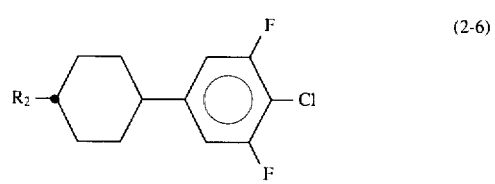

(2-6)

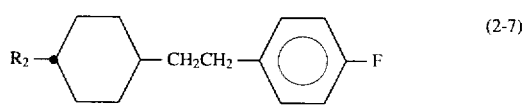

(2-7)

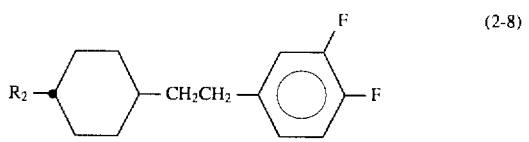

(2-8)

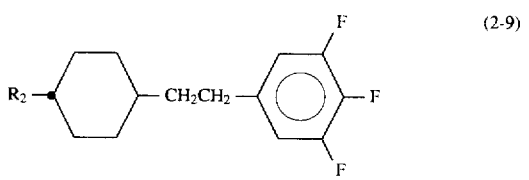

(2-9)

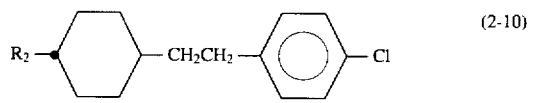

(2-10)

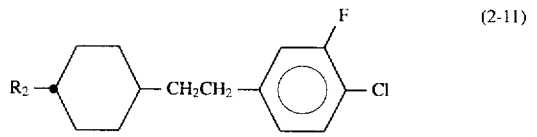

(2-11)

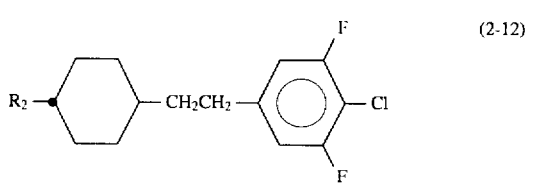

(2-12)

($R_2$ is as defined above.)

Among the second component, as preferable examples of compounds included in the formula (3), the following (3-1) to (3-18) are, mentioned:

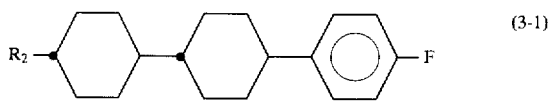

(3-1)

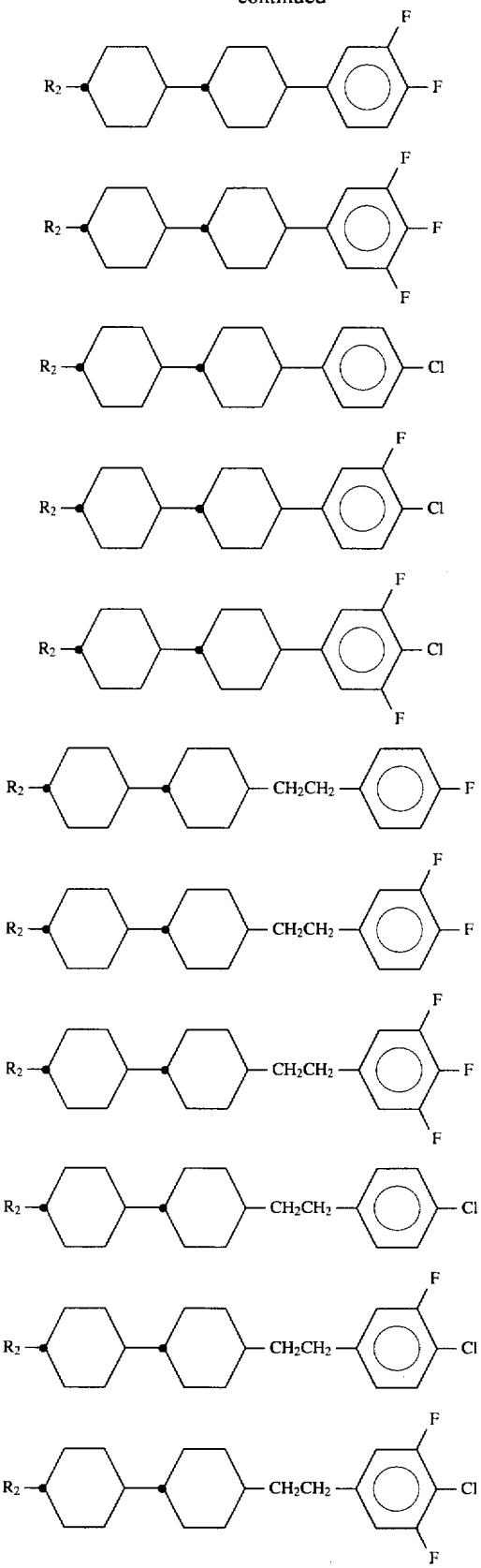
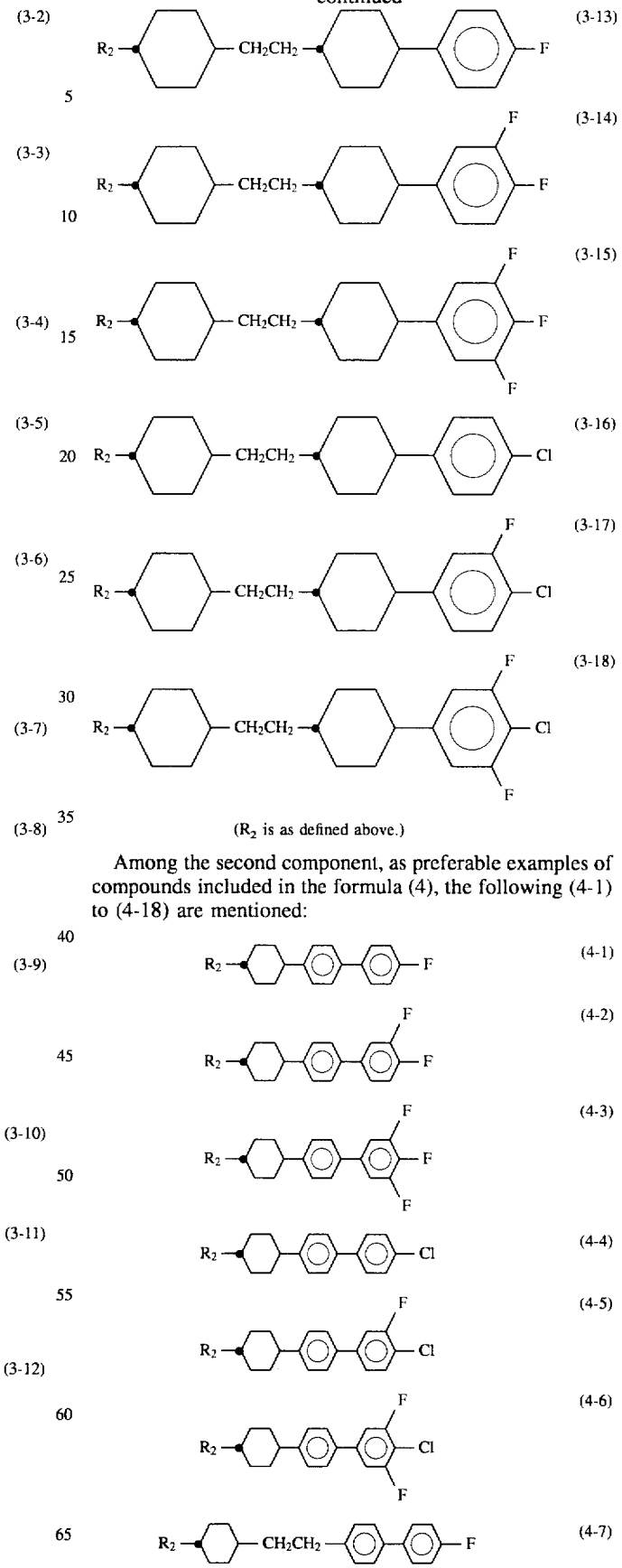
(R₂ is as defined above.)
Among the second component, as preferable examples of compounds included in the formula (4), the following (4-1) to (4-18) are mentioned:

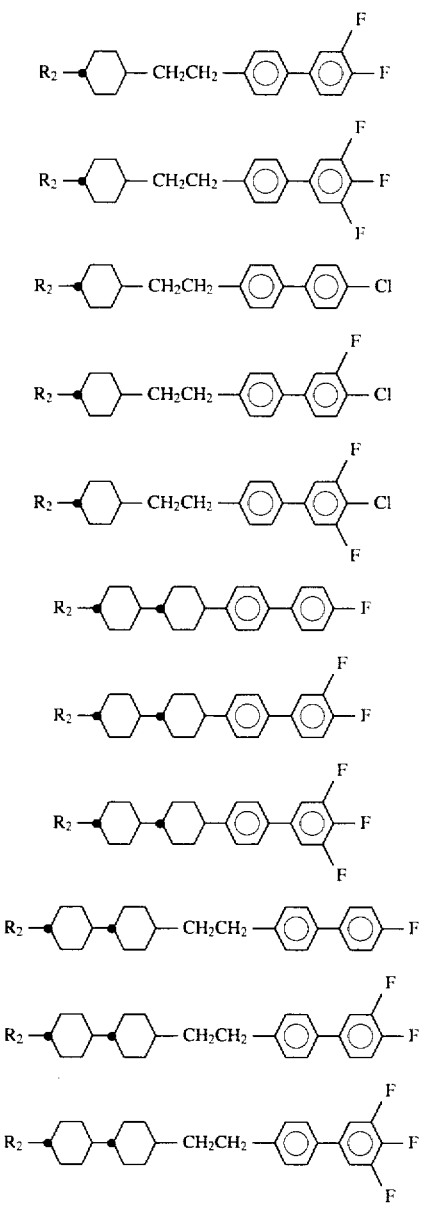

(R₂ is as defined above.)

These compounds expressed by the formulas (2) to (4) are those having a positive dielectric anisotropy and have a far superior thermal stability and chemical stability. Thus, the compounds are indispensable in the case where a liquid crystal composition for TFT (AM-LCD), for which particularly a high voltage-holding ratio and a larger specific resistance value with a high reliability are required.

The quantity of the compounds used is suitably within a range of 1 to 99% by weight based upon the total weight of the liquid crystal composition in the case where a liquid crystal composition for TFT is prepared, and preferably 10 to 97% by weight, more preferably 40 to 95% by weight. Further, at that time, the compound expressed by the formulas (5) to (9) may be partly contained. In addition, in the case where a liquid crystal composition for STN display mode or usual TN display mode is prepared, too, it is possible to use compounds expressed by the formulas (2) to (4).

Next, among the above second component, as preferable examples of compounds included in the formula (5), the following (5-1) to (5-17) are mentioned:

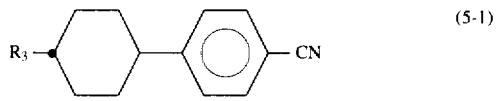
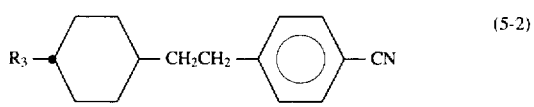
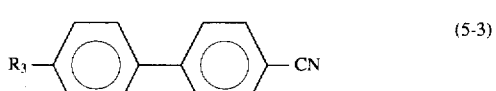
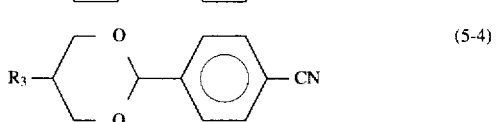
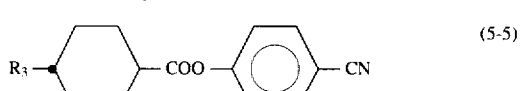
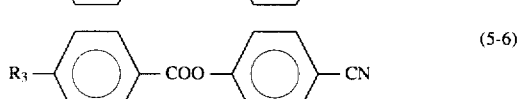
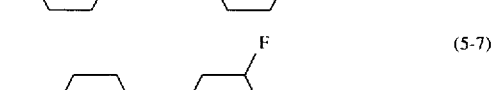
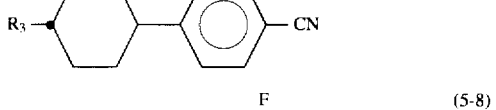
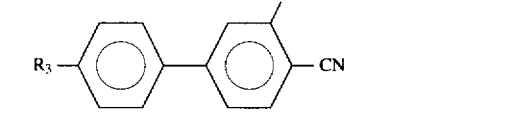
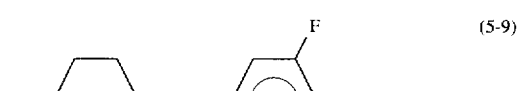
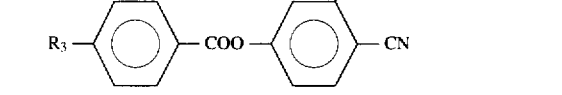

-continued

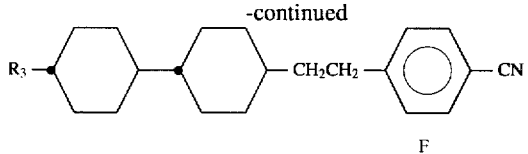 (5-13)

 (5-14)

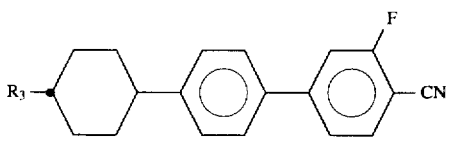 (5-15)

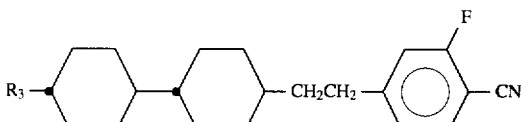 (5-16)

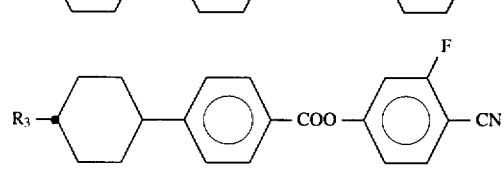 (5-17)

($R_3$ is as defined above.)

Among the second component, as preferable examples of compounds included in the formula (6), the following (6-1) to (6-3) are mentioned.

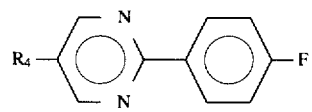 (6-1)

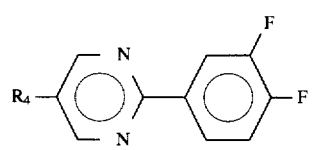 (6-2)

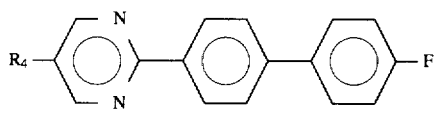 (6-3)

($R_4$ is as defined above.)

Among the second component, as preferable examples of compounds included in the formula (7), the following (7-1) to (7-9) are mentioned:

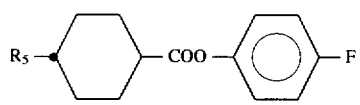 (7-1)

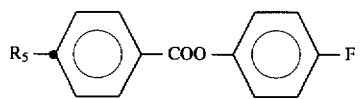 (7-2)

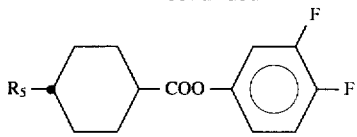 (7-3)

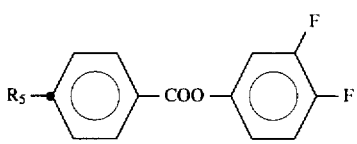 (7-4)

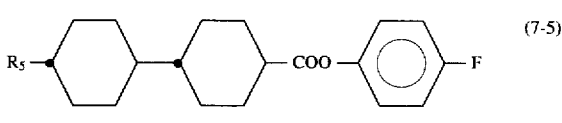 (7-5)

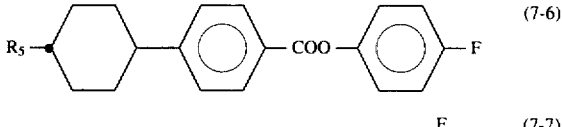 (7-6)

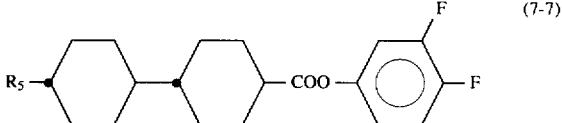 (7-7)

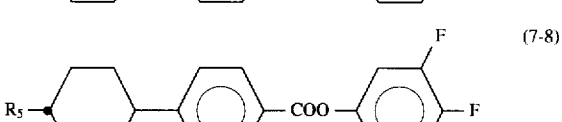 (7-8)

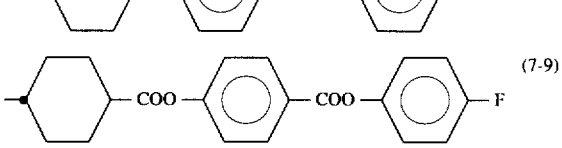 (7-9)

($R_5$ is as defined above.)

Compounds expressed by the formulas (5) to (7) have a positive and large dielectric anisotropy value; hence they can be used particularly for reducing the threshold voltage of the liquid crystal composition. Further, they can be also used for adjusting the viscosity and Δn, and besides for broadening the nematic temperature range by raising the clearing point or by other means, and further for improving the steepness.

Among the second component, as preferable examples of compounds included in the formula (8), the following (8-1) to (8-6) can be mentioned:

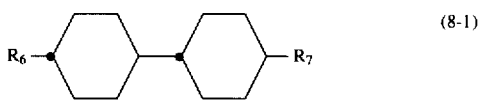 (8-1)

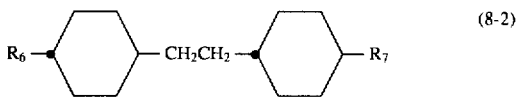 (8-2)

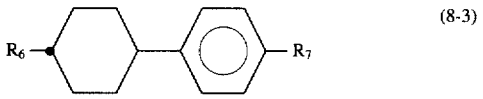 (8-3)

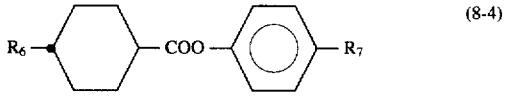 (8-4)

-continued

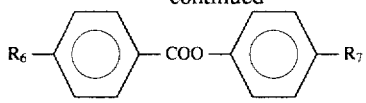
(8-5)

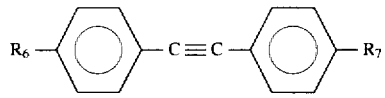
(8-6)

($R_6$ and $R_7$ are each as defined above.)

Further, among the second component, as preferable examples of compounds included in the following (9-1) to (9-10) can be mentioned:

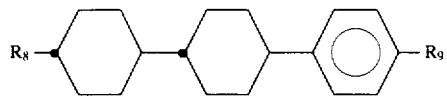
(9-1)

(9-2)

(9-3)

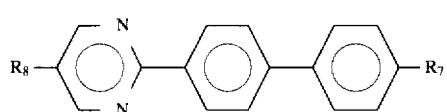
(9-4)

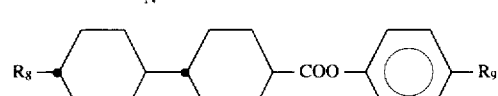
(9-5)

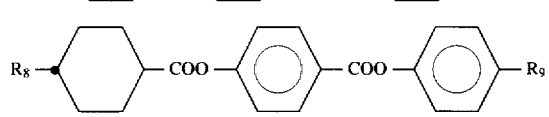
(9-6)

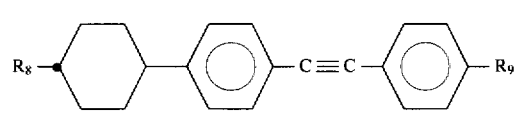
(9-7)

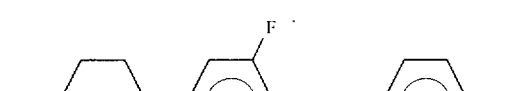
(9-8)

(9-9)

(9-10)

($R_8$ and $R_9$ are each as defined above.)

Compounds expressed by the formulas (8) and (9) are those having a negative or weak, positive dielectric anisotropy. Among them, compound of the formula (8) can be used mainly for the viscosity reduction and/or $\Delta n$ adjustment of liquid crystal composition. Further, compound of the formula (9) can be used for broadening the nematic temperature range by raising the clearing point or by other means and/or for adjusting the $\Delta n$.

Among the second component, compounds expressed by the above formulas (5) to (9) are indispensable particularly for preparing liquid crystal compositions for STN display mode or usual TN display mode.

In this case, the quantity of the compounds used is suitably within a range of 1 to 99% by weight based upon the total weight of the liquid crystal composition, preferably 10 to 97% by weight, more preferably 40 to 95% by weight.

Further, at that time, compounds expressed by the formulas (2) to (4) may be partly used.

Next, (B), (C), (D) and/or (E) are added to the liquid crystal composition in accordance with the object, and examples of compounds included therein are as follows:

Firstly, as preferable examples of compounds included in (B), the following (B1) to (B13) can be mentioned:

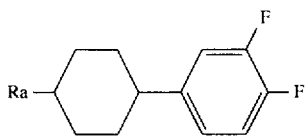
(B1)

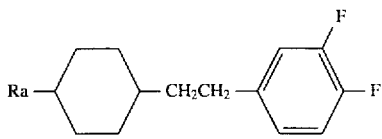
(B2)

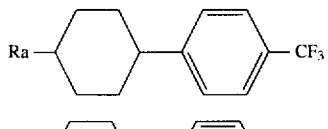
(B3)

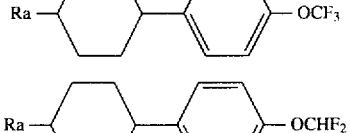
(B4)

(B5)

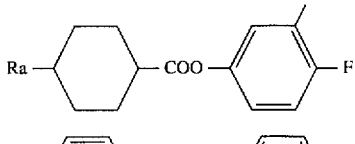
(B6)

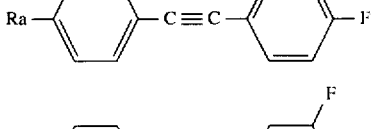
(B7)

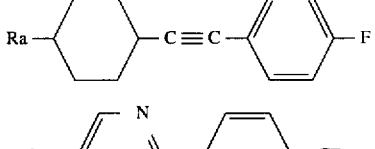
(B8)

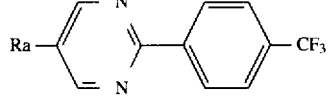
(B9)

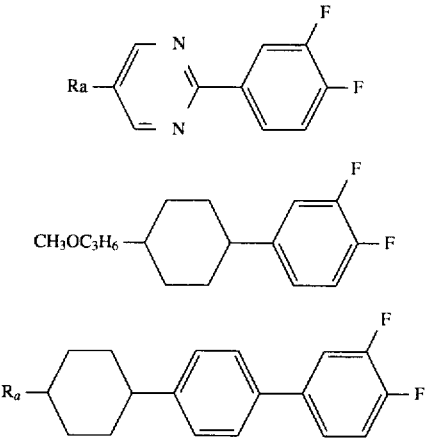
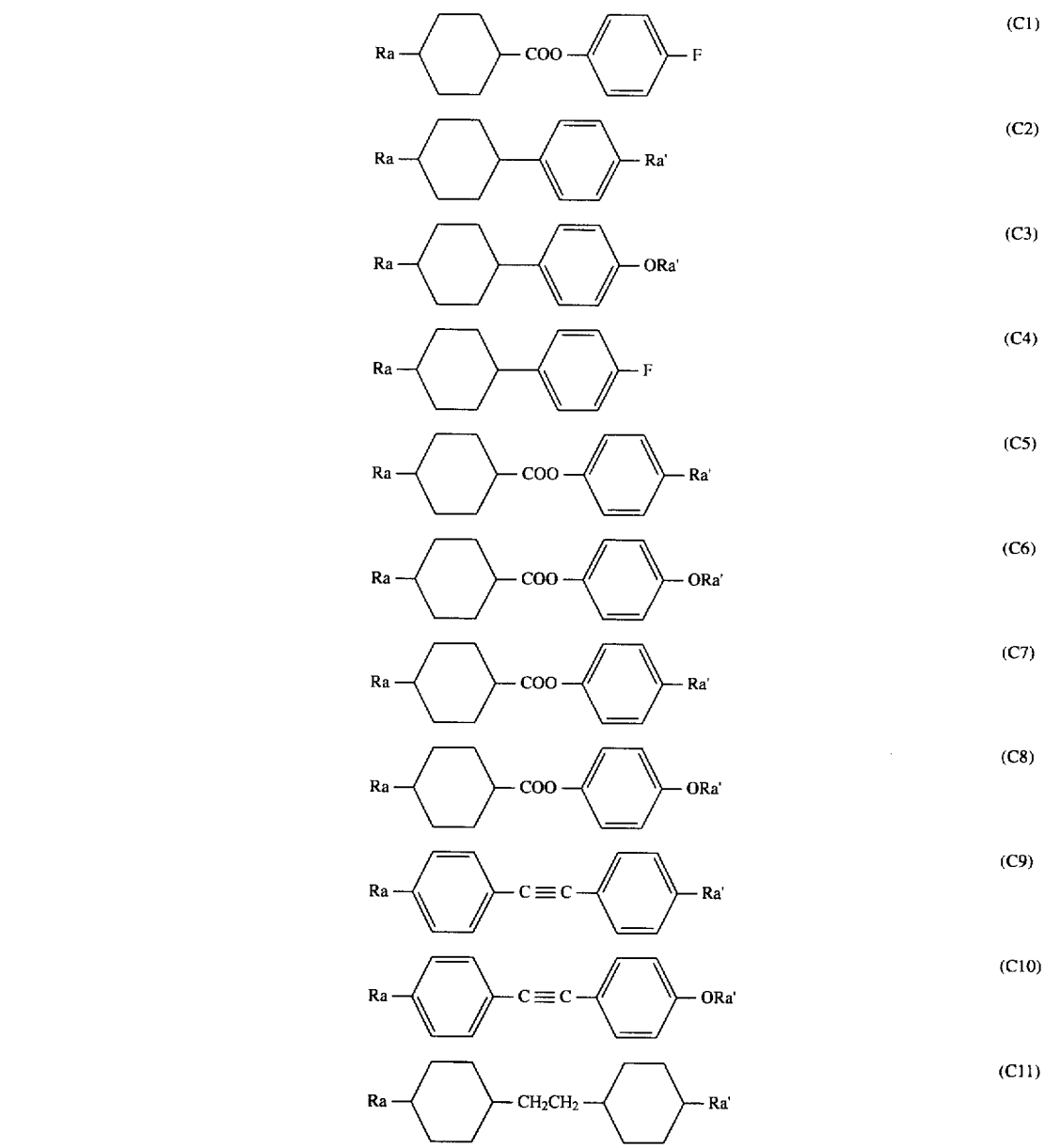
(In the above compounds, Ra represents an alkyl group or an alkenyl group of 1 to 10 carbon atoms, but one or two or more not adjacent carbon atoms therein may be replaced by oxygen atom.)
Further, as preferable examples of compounds included in (C), the following (C1) to (C34) can be mentioned:

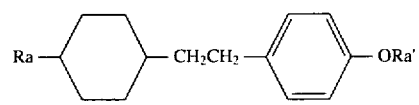 (C12)
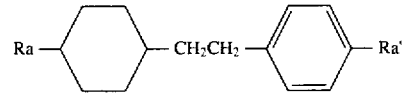 (C13)
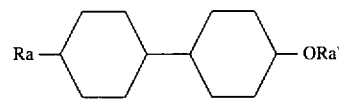 (C14)
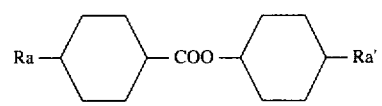 (C15)
 (C16)
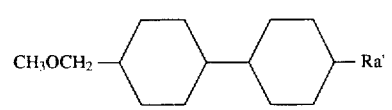 (C17)
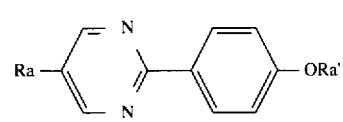 (C18)
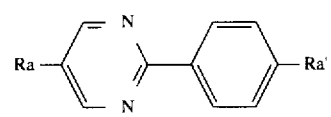 (C19)
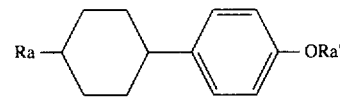 (C20)
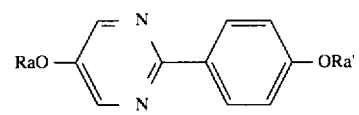 (C21)
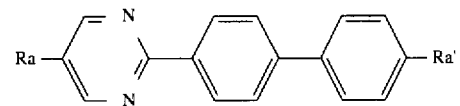 (C22)
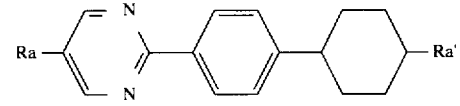 (C23)
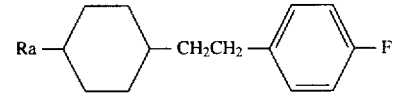 (C24)
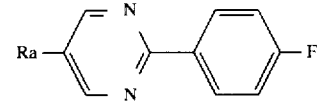 (C25)

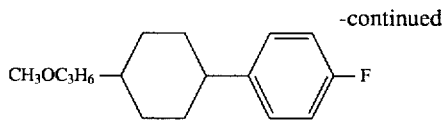 (C26)
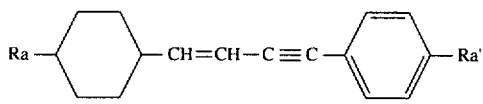 (C27)
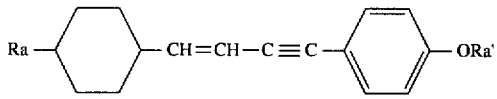 (C28)
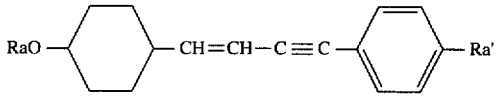 (C29)
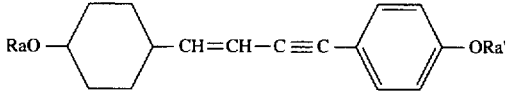 (C30)
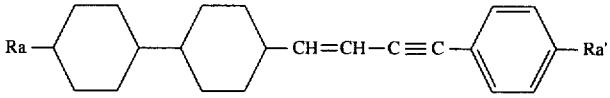 (C31)
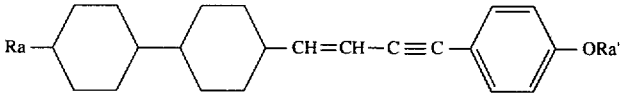 (C32)
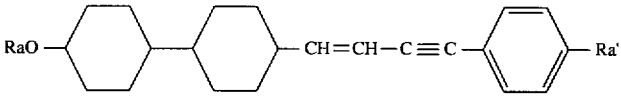 (C33)
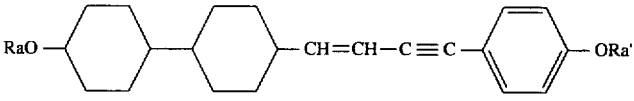 (C34)
(In the above compounds, Ra and Ra' each represent an alkyl group or an alkenyl group of 1 to 10 carbon atoms, and one or two or more not adjacent carbon atoms therein may be replaced by oxygen atom.)
Further, as preferable examples of compounds included in (D), the following (D1) to (D57) can be mentioned:
 (D1)
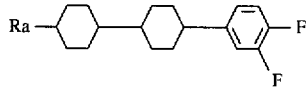 (D2)
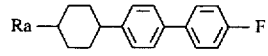 (D3)
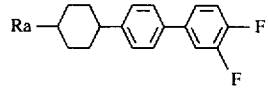 (D4)
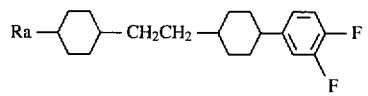 (D5)
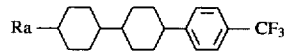 (D6)
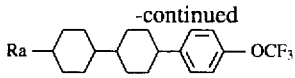 (D7)
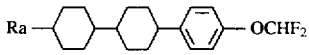 (D8)
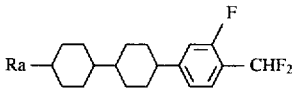 (D9)
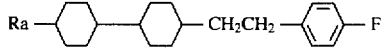 (D10)
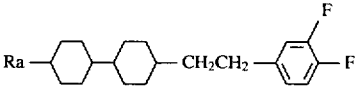 (D11)
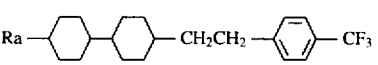 (D12)
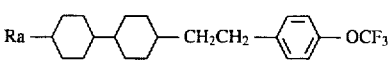 (D13)
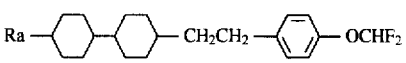 (D14)
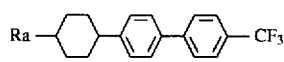 (D15)

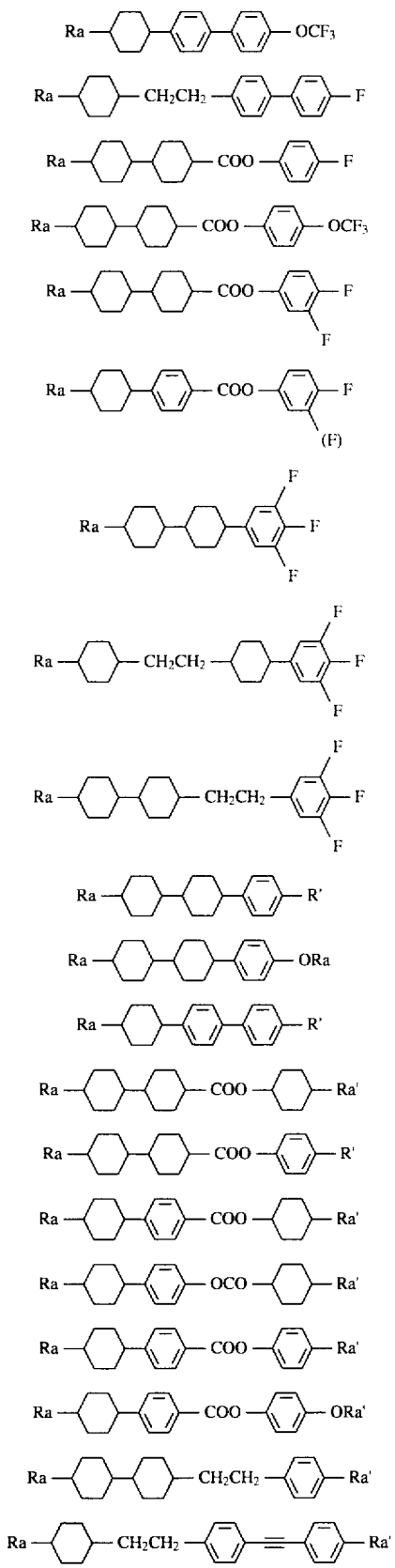
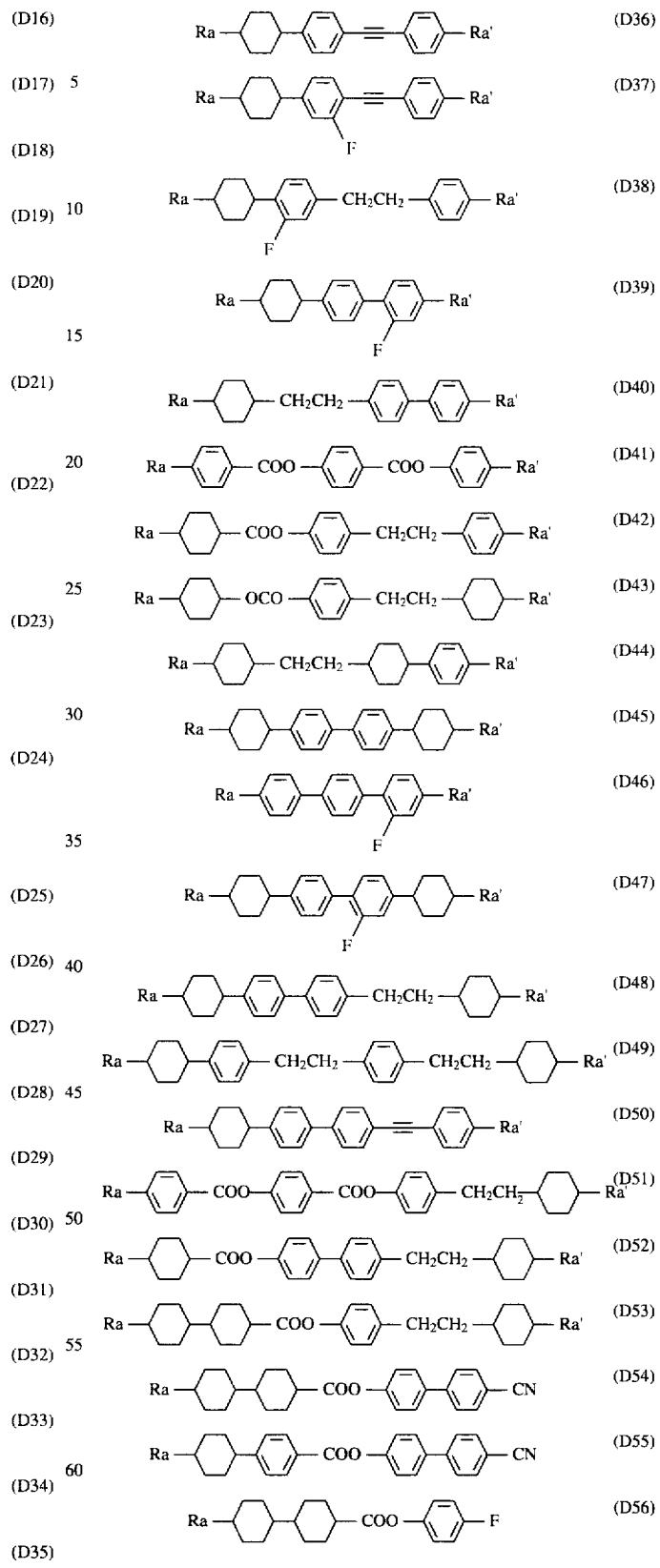

-continued

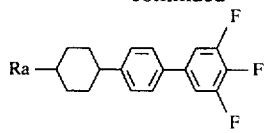 (D57)

(In the above compounds, Ra and Ra' are each as defined above.)

Further, as preferable examples of compounds included in (E), the following (E1) to (E18) can be mentioned:

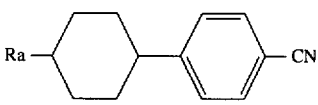 (E1)

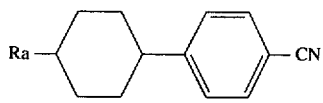 (E2)

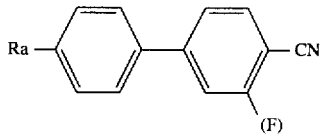 (E3)

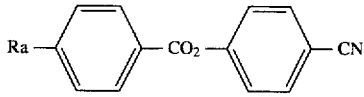 (E4)

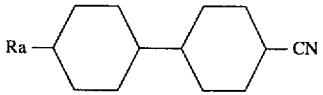 (E5)

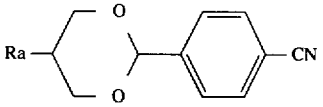 (E6)

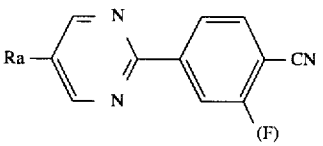 (E7)

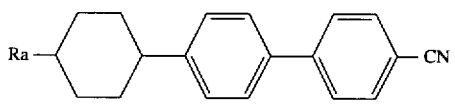 (E8)

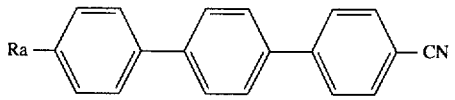 (E9)

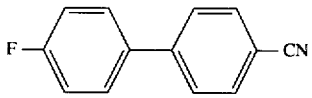 (E10)

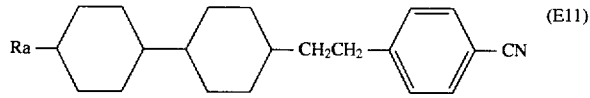 (E11)

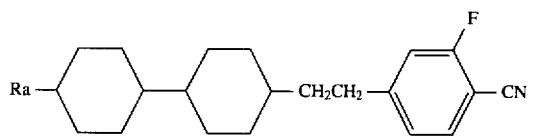 (E12)

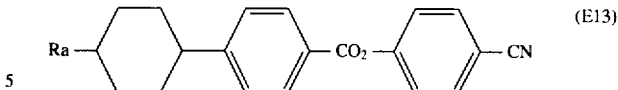 (E13)

 (E14)

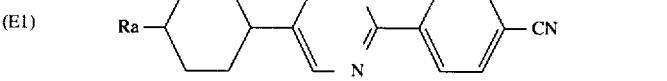 (E15)

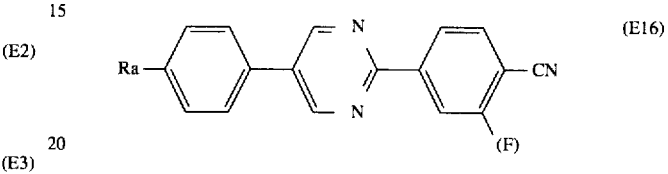 (E16)

 (E17)

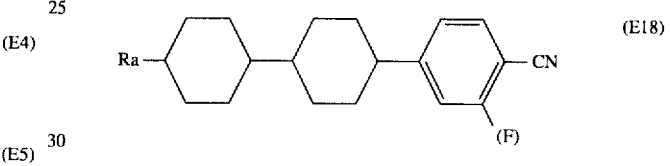 (E18)

(In the above compounds, Ra is as defined above.)

As to the liquid crystal compositions of the present invention, it is preferred to contain one or more compounds expressed by the formula (1) in a proportion of 0.1 to 99% by weight, in order to exhibit superior characteristics.

When the liquid crystal compositions are used for TFT liquid crystal display elements, it is possible to improve steepness and viewing angle. Further, since the compound of the formula (1) is a low viscosity compound, the response speed of liquid crystal display elements using the compound is improved.

The liquid crystal composition of the present invention is prepared generally according to known process, for example, a process of mixing various components at a high temperature and dissolving in each other. Further, if necessary, a suitable additive is added, whereby improvement is carried out in accordance with aimed use applications, to optimize the compositions. Such additives have been well known by person of ordinary skill in the art, and have been described in literatures or the like in detail. Usually, a chiral dopant inducing the helical structure of liquid crystals to thereby adjust necessary twisted angle and prevent reverse twist.

As examples of the liquid crystal compositions containing the compound of the present invention, the following can be mentioned, and in addition, the compound Nos. are the same as those shown in the following Examples:

Composition example 1
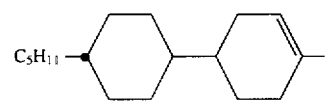 (compound No. 3) 10%
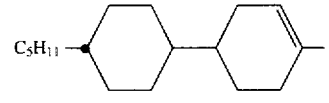 (compound No. 9) 10%
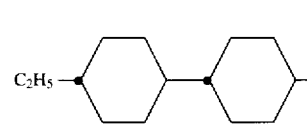 8%
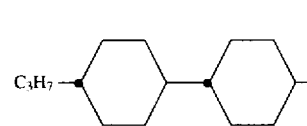 8%
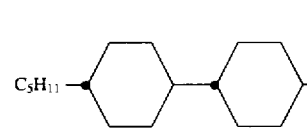 8%
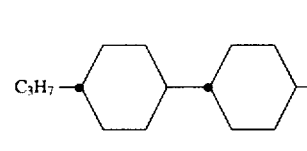 6%
 5%
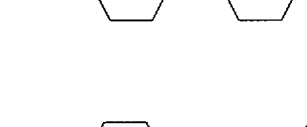 5%
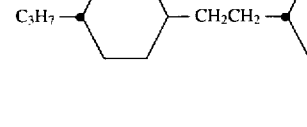 5%
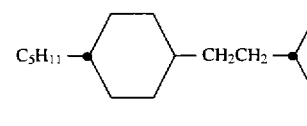 5%

-continued
Composition example 1
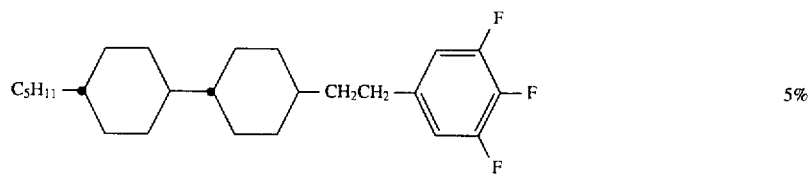 5%
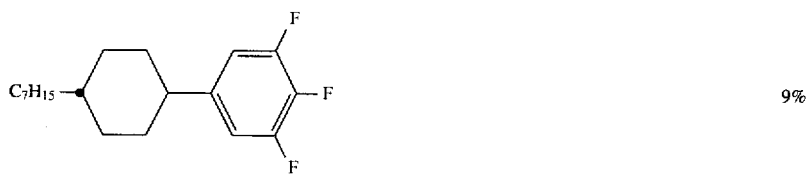 9%
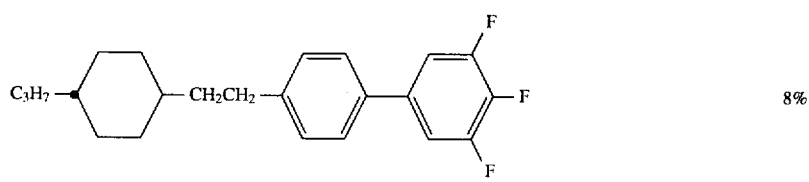 8%
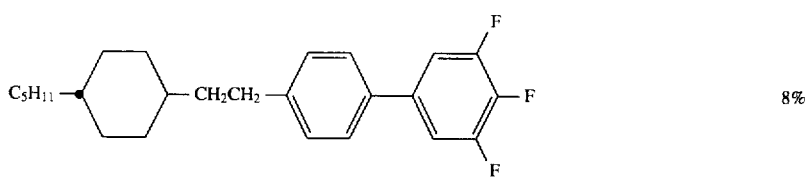 8%
Composition example 2
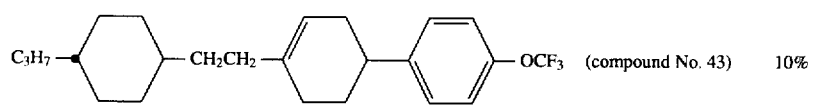 (compound No. 43) 10%
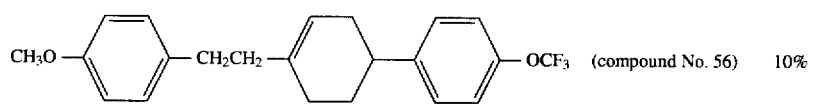 (compound No. 56) 10%
 5%
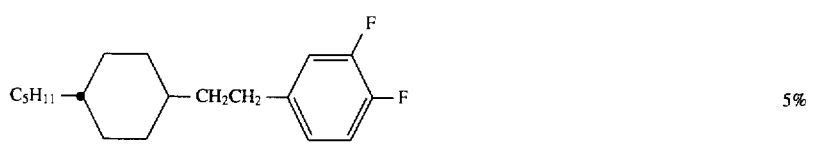 5%
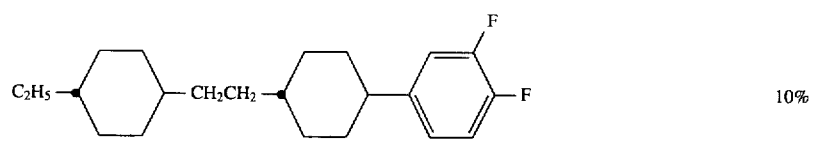 10%
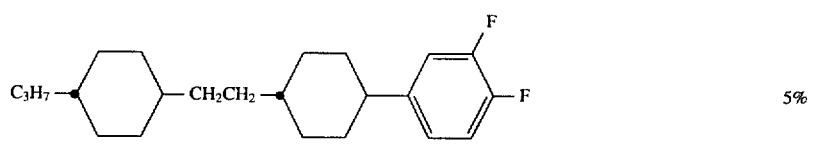 5%

-continued
Composition example 2
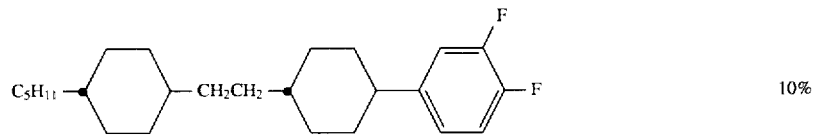 10%
 5%
 5%
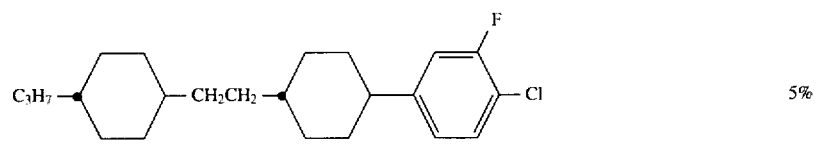 5%
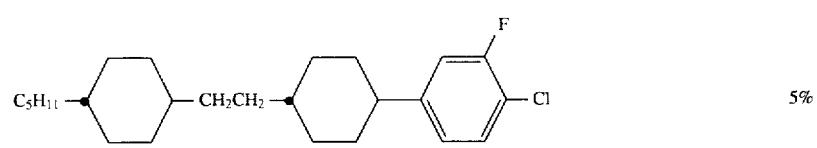 5%
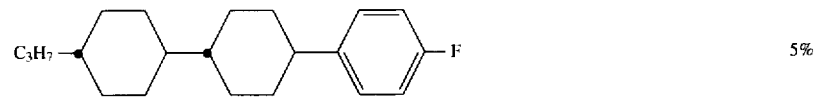 5%
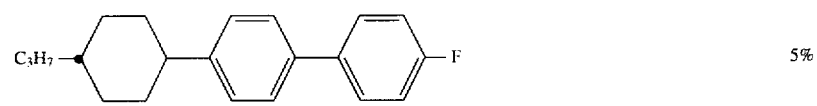 5%
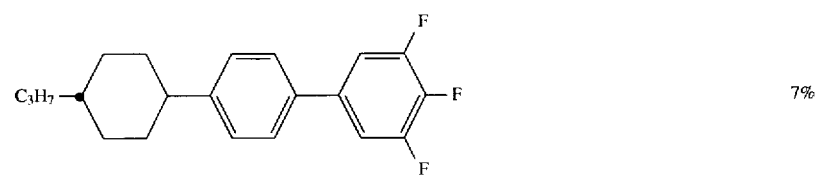 7%
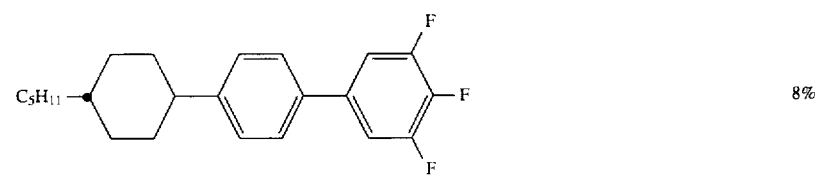 8%
Composition example 3
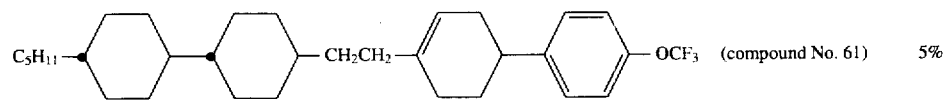 (compound No. 61)   5%

-continued
Composition example 3

| Structure | | Percentage |
|---|---|---|
| C₃H₇-[Cy]-[Cy]-CH₂CH₂-[Ph(2-F,5-F)]-CF₃ | (compound No. 6) | 10% |
| C₃H₇-[Cy]-[Cy]-CH₂CH₂-[Ph(3-F)]-OCF₃ | (compound No. 11) | 10% |
| C₂H₅-[Cy]-[Cy]-[Ph(3,4-F₂)] | | 7% |
| C₃H₇-[Cy]-[Cy]-[Ph(3,4-F₂)] | | 7% |
| C₅H₁₁-[Cy]-[Cy]-[Ph(3,4-F₂)] | | 7% |
| C₂H₅-[Cy]-[Ph]-[Ph(3,4-F₂)] | | 5% |
| C₃H₇-[Cy]-[Ph]-[Ph(3,4-F₂)] | | 5% |
| C₅H₁₁-[Cy]-[Ph]-[Ph(3,4-F₂)] | | 10% |
| C₃H₇-[Cy]-[Ph]-[Ph(3,4,5-F₃)] | | 5% |
| C₅H₁₁-[Cy]-[Ph]-[Ph(3,4,5-F₃)] | | 4% |

-continued
Composition example 3
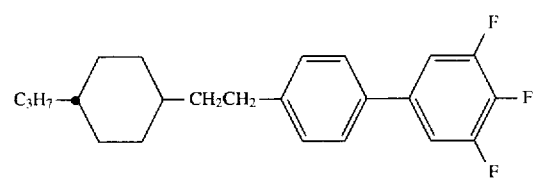 5%
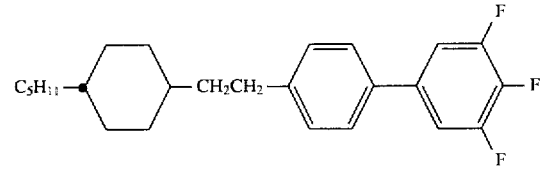 5%
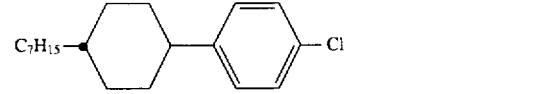 5%
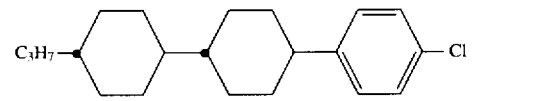 5%
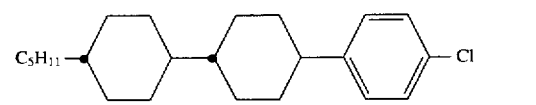 5%
Composition example 4
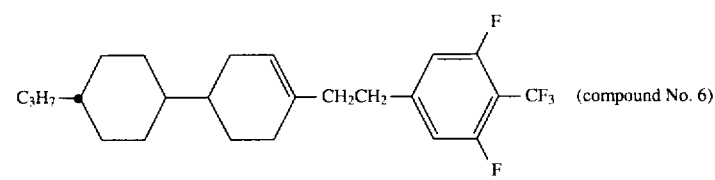 (compound No. 6) 7%
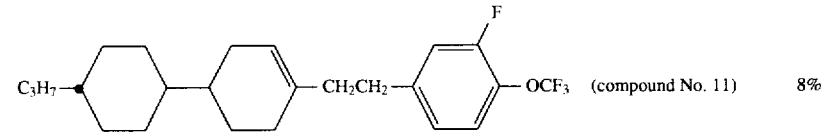 (compound No. 11) 8%
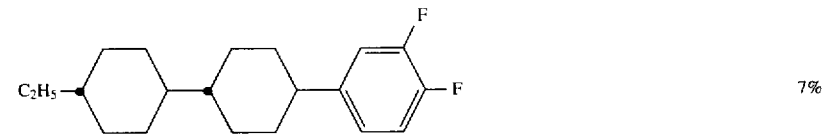 7%
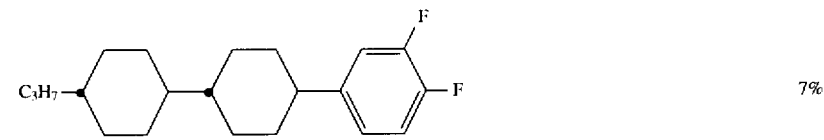 7%
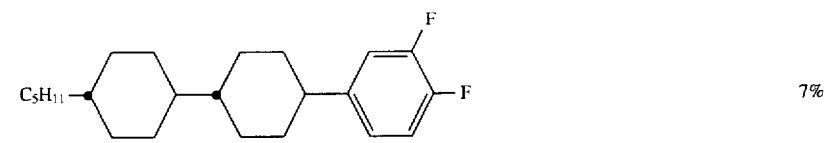 7%

-continued
Composition example 4
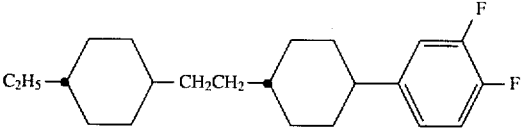 10%
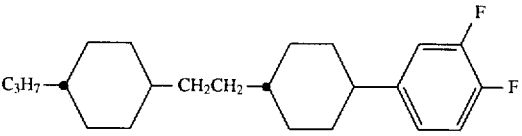 5%
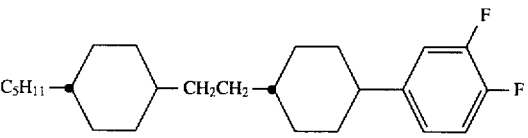 10%
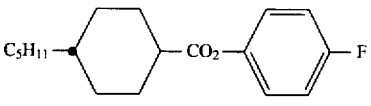 5%
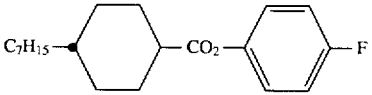 4%
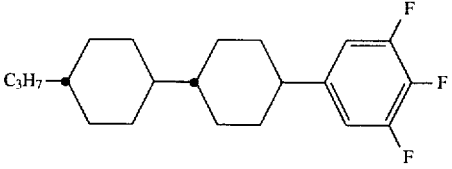 5%
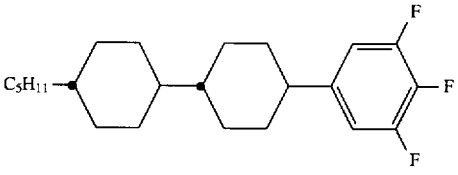 5%
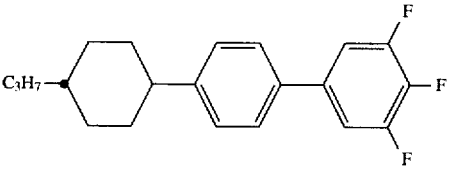 5%
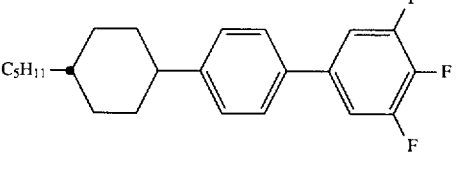 5%
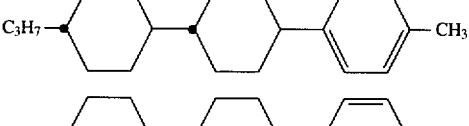 5%
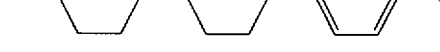 5%

Composition example 5

| Structure | | Percentage |
|---|---|---|
| C₅H₁₁–[Cy]–[Cy=]–CH₂CH₂–[Ph]–OCF₃ | (compound No. 9) | 8% |
| C₃H₇–[Cy]–CH₂CH₂–[Cy=]–[Ph]–OCF₃ | (compound No. 43) | 8% |
| CH₃O–[Ph]–CH₂CH₂–[Cy=]–[Ph]–OCF₃ | (compound No. 56) | 9% |
| C₅H₁₁–[Cy]–[Ph]–Cl | | 5% |
| C₇H₁₅–[Cy]–[Ph]–Cl | | 5% |
| C₂H₅–[Cy]–[Cy]–[Ph]–Cl | | 8% |
| C₃H₇–[Cy]–[Cy]–[Ph]–Cl | | 8% |
| C₅H₁₁–[Cy]–[Cy]–[Ph]–Cl | | 8% |
| C₃H₇–[Cy]–[Cy]–[Ph(3,4,5-F₃)] | | 5% |
| C₅H₁₁–[Cy]–[Cy]–[Ph(3,4,5-F₃)] | | 5% |
| C₃H₇–[Cy]–[Ph]–[Ph(3,4,5-F₃)] | | 5% |
| C₅H₁₁–[Cy]–[Ph]–[Ph(3,4,5-F₃)] | | 5% |

-continued
Composition example 5
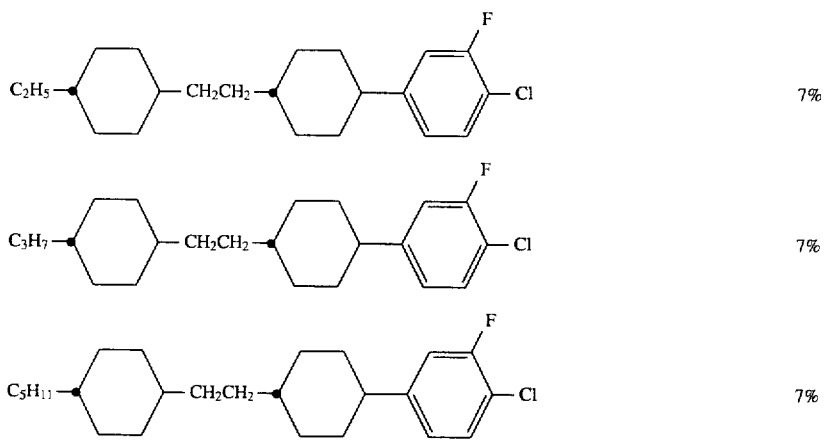
| | |
|---|---|
| (first structure) | 7% |
| (second structure) | 7% |
| (third structure) | 7% |
Composition example 6
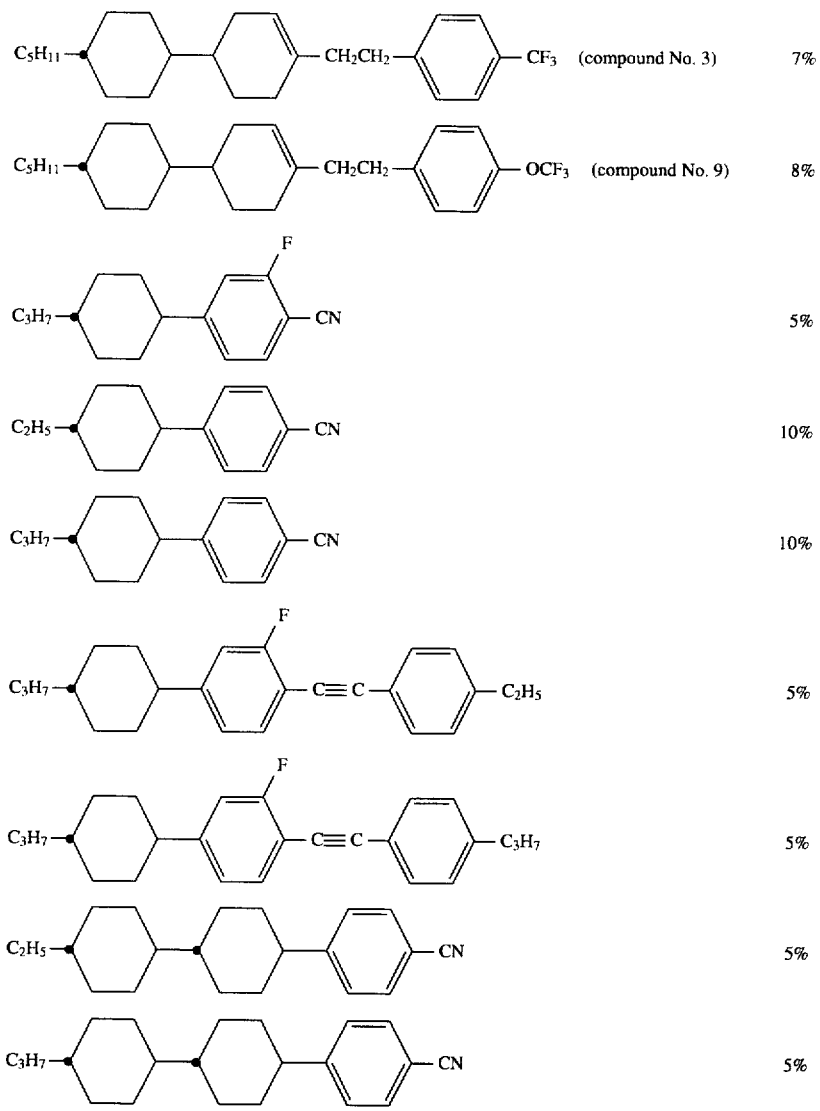
| | | |
|---|---|---|
| (compound No. 3) | | 7% |
| (compound No. 9) | | 8% |
| | | 5% |
| | | 10% |
| | | 10% |
| | | 5% |
| | | 5% |
| | | 5% |
| | | 5% |

Composition example 6

| Structure | % |
|---|---|
| C₃H₇–[Cy]–[Cy]–CO₂–[Ph]–F | 5% |
| C₅H₁₁–[Cy]–[Cy]–CO₂–[Ph]–F | 5% |
| C₃H₇–[Cy]–[Cy]–[Ph]–OCH₃ | 5% |
| C₃H₇–[Cy]–[Cy]–[Ph]–CH₃ | 5% |
| C₃H₇–[Cy]–[Cy]–[Ph]–C₃H₇ | 5% |
| C₂H₅–[Cy]–[Cy]–[Ph(3,4-diF)] | 5% |
| C₃H₇–[Cy]–[Cy]–[Ph(3,4-diF)] | 5% |
| C₅H₁₁–[Cy]–[Cy]–[Ph(3,4-diF)] | 5% |

Composition example 7

| Structure | | % |
|---|---|---|
| C₃H₇–[Cy]–CH₂CH₂–[Cy]–[Ph]–OCF₃ | (compound No. 43) | 7% |
| CH₃O–[Ph]–CH₂CH₂–[Cy]–[Ph]–OCF₃ | (compound No. 56) | 8% |
| CH₂=CHCH₂–[Cy]–[Ph]–CN | | 10% |
| CH₃CH=CHCH₂–[Cy]–[Ph]–CN | | 10% |

-continued
Composition example 7

| Structure | % |
|---|---|
| C₃H₇–[Cy]–[Ph]–CN | 10% |
| CH₃OCH₂–[Cy]–[Ph]–CN | 5% |
| CH₃OCH₂–[Cy]–[Cy]–C₃H₇ | 7% |
| C₃H₇–[Cy]–[Cy]–C₄H₉ | 8% |
| C₂H₅–[Ph]–C≡C–[Ph]–OCH₃ | 3% |
| C₃H₇–[Ph]–C≡C–[Ph]–OCH₃ | 3% |
| C₄H₉–[Ph]–C≡C–[Ph]–OCH₃ | 3% |
| C₄H₉–[Ph]–C≡C–[Ph]–OC₂H₅ | 3% |
| C₅H₁₁–[Ph]–C≡C–[Ph]–OCH₃ | 3% |
| C₃H₇–[Cy]–[Cy]–[Ph]–OCH₃ | 5% |
| C₃H₇–[Cy]–[Cy]–[Ph]–F | 5% |
| C₃H₇–[Cy]–[Cy]–[Ph]–CH₃ | 5% |
| C₃H₇–[Cy]–[Cy]–[Ph]–C₃H₇ | 5% |

Composition example 8

| Structure | | % |
|---|---|---|
| C₅H₁₁–[Cy]–[Cy]–CH₂CH₂–[Ph]–CF₃ | (compound No. 3) | 6% |

-continued
Composition example 8

| Structure | | |
|---|---|---|
| C₅H₁₁–[Cy]–[Cy]–CH₂CH₂–[Ph]–OCF₃ | (compound No. 9) | 7% |
| C₃H₇–[Cy]–CH₂CH₂–[Cy]–[Ph]–OCF₃ | (compound No. 43) | 7% |
| C₅H₁₁–[pyrimidine]–[Ph(3,4-F)]–CN | | 10% |
| C₅H₅–[Cy]–[Ph(3-F)]–CN | | 10% |
| C₃H₇–[Cy]–[Ph(3-F)]–CN | | 5% |
| C₂H₅–[Ph]–[Ph]–CN | | 10% |
| C₃H₇–[Cy]–[Ph]–CN | | 5% |
| C₂H₅–[Cy]–[Cy]–[Ph]–CN | | 5% |
| C₃H₇–[Cy]–[Cy]–[Ph]–CN | | 5% |
| C₄H₉–[Cy]–[Cy]–[Ph]–CN | | 5% |
| C₃H₇–[Cy]–[Cy]–[Ph]–CH₃ | | 5% |
| C₂H₅–[Cy]–[Cy]–[Ph(3-F)]–CN | | 5% |
| C₃H₇–[Cy]–[Cy]–[Ph(3-F)]–CN | | 5% |

-continued
Composition example 8
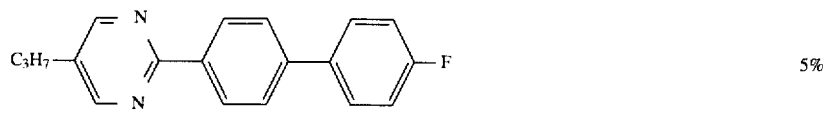 5%
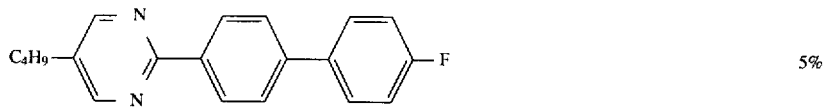 5%
Composition example 9
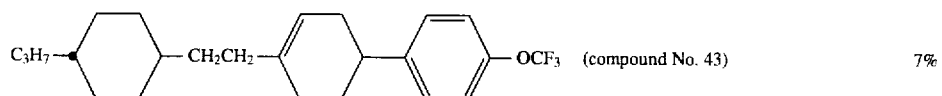 (compound No. 43)  7%
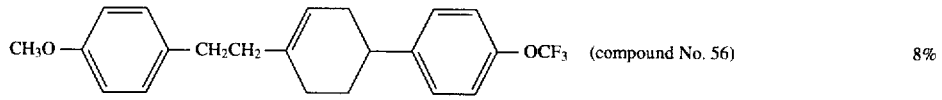 (compound No. 56)  8%
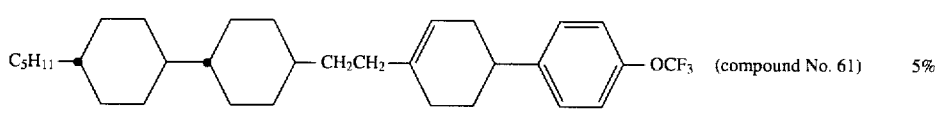 (compound No. 61)  5%
 10%
 10%
 8%
 8%
 5%
 5%
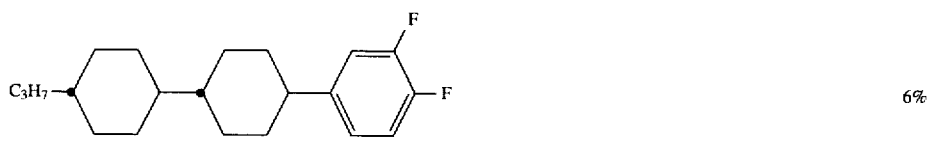 6%

-continued
Composition example 9
 5%
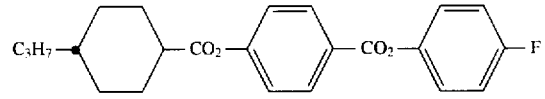 5%
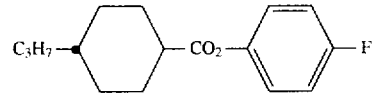 5%
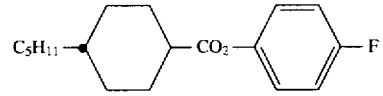 5%
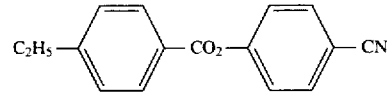 4%
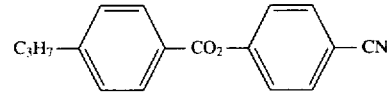 4%
Composition example 10
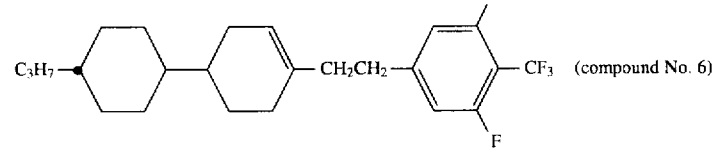 (compound No. 6)   7%
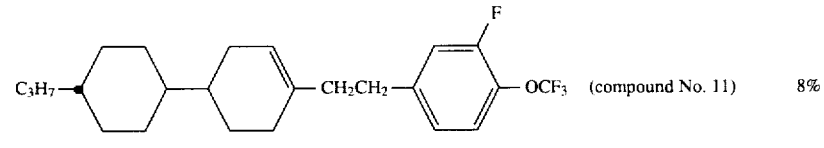 (compound No. 11)   8%
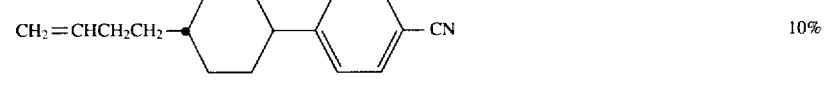 10%
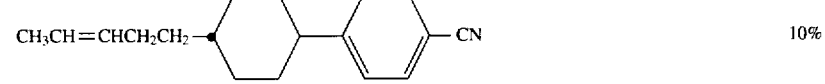 10%
 5%
 5%

-continued
Composition example 10
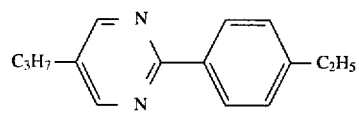 5%
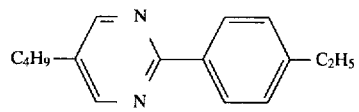 5%
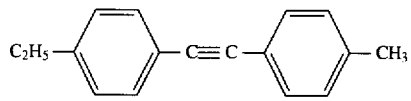 3%
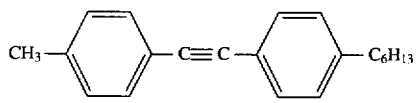 6%
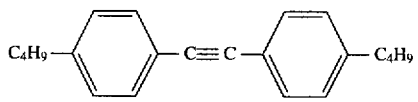 3%
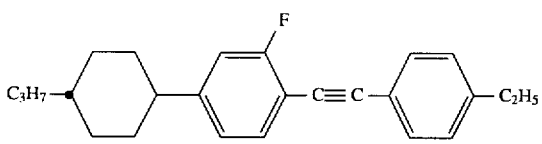 4%
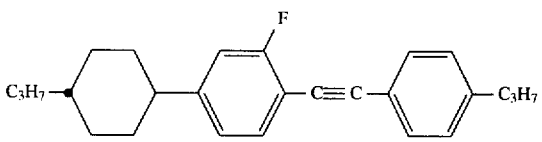 4%
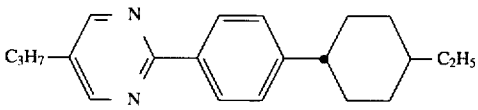 5%
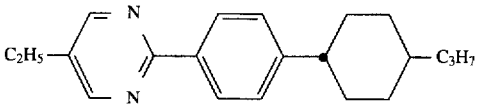 5%
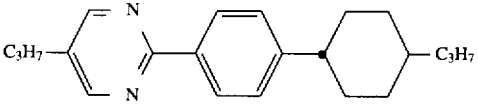 5%
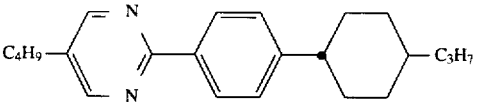 5%
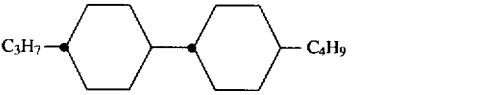 5%

Composition example 11
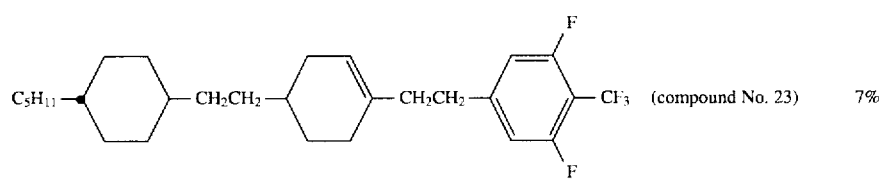 (compound No. 23) 7%
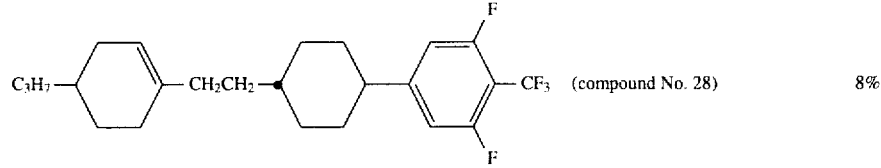 (compound No. 28) 8%
 5%
 5%
 5%
 5%
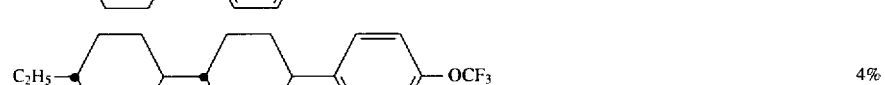 4%
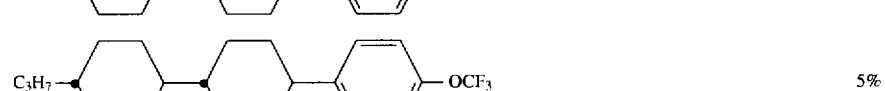 5%
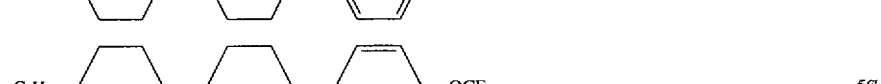 5%
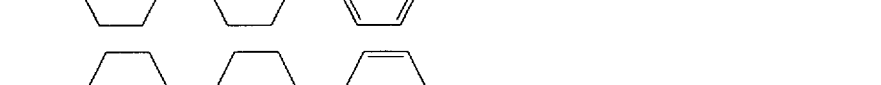 6%
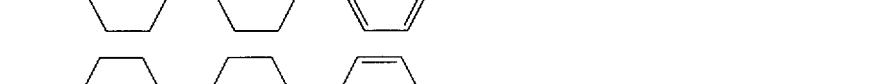 5%
 5%
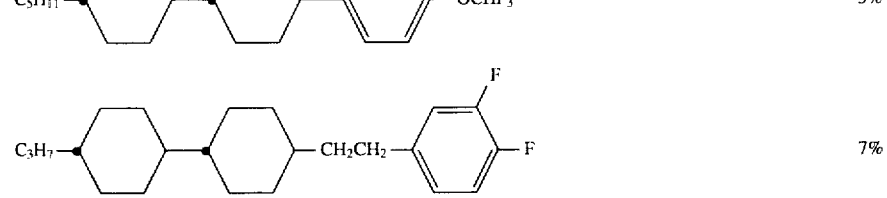 7%

-continued
Composition example 11
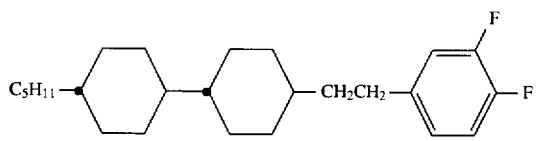 8%
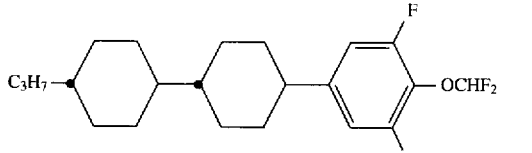 9%
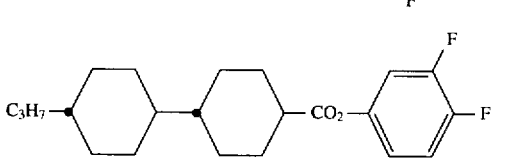 5%
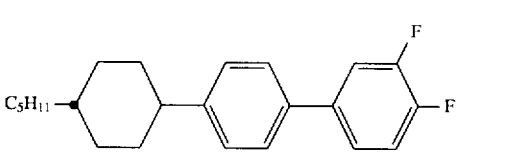 3%
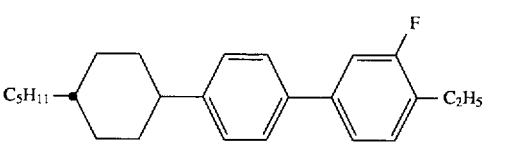 3%
Composition example 12
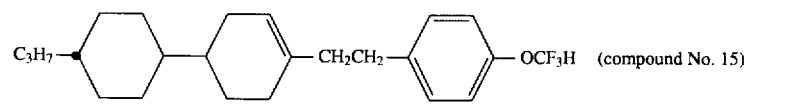 (compound No. 15)    7%
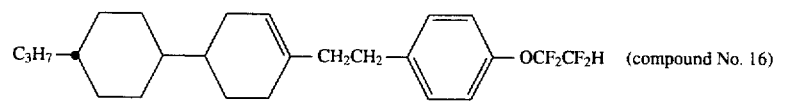 (compound No. 16)    7%
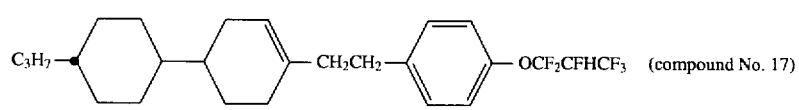 (compound No. 17)    6%
 9%
 8%
 8%
 7%

-continued
Composition example 12
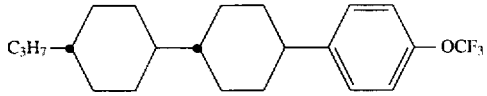 5%
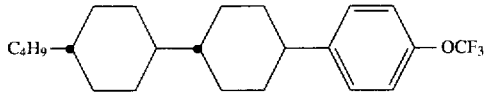 5%
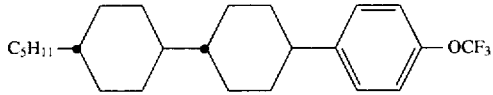 5%
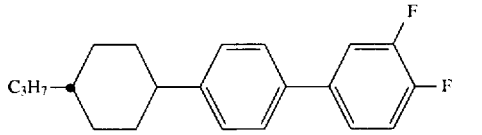 7%
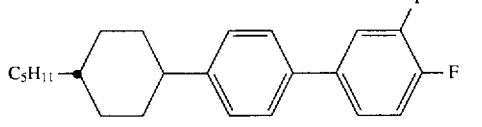 7%
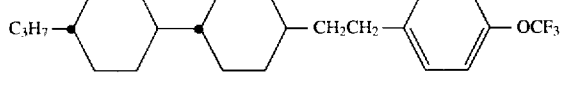 5%
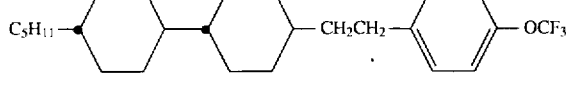 5%
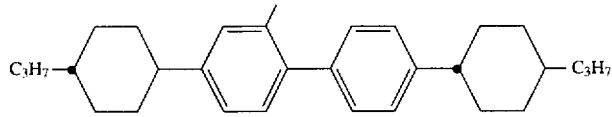 3%
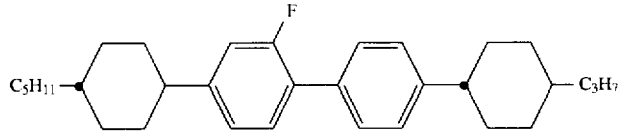 3%
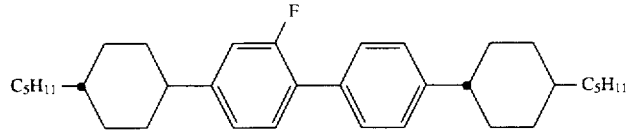 3%
Composition example 13
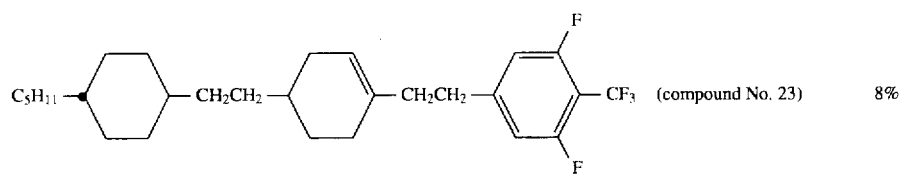 (compound No. 23)  8%

-continued
Composition example 13
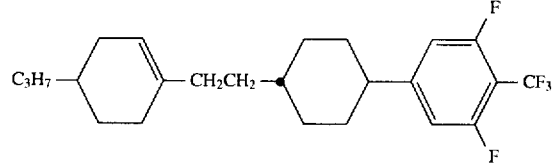 (compound No. 28)  7%
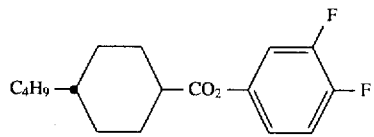  8%
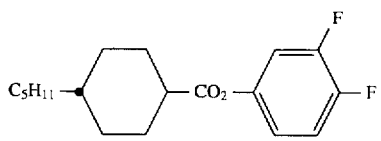  7%
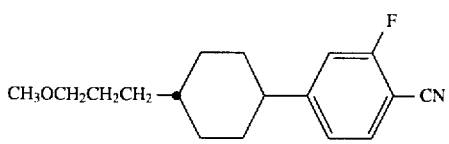  10%
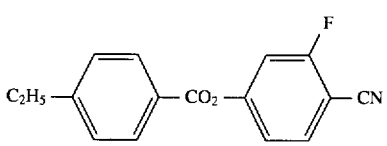  4%
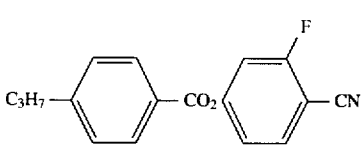  4%
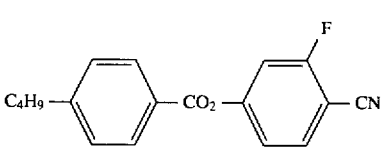  6%
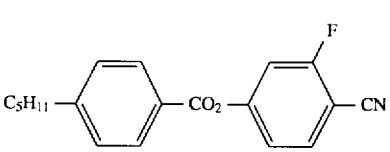  6%
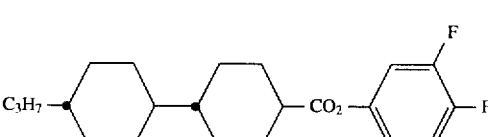  5%
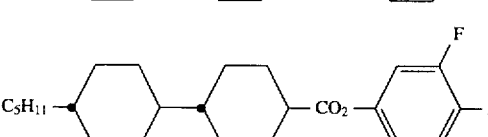  5%
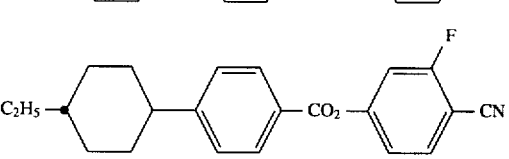  5%

-continued
Composition example 13

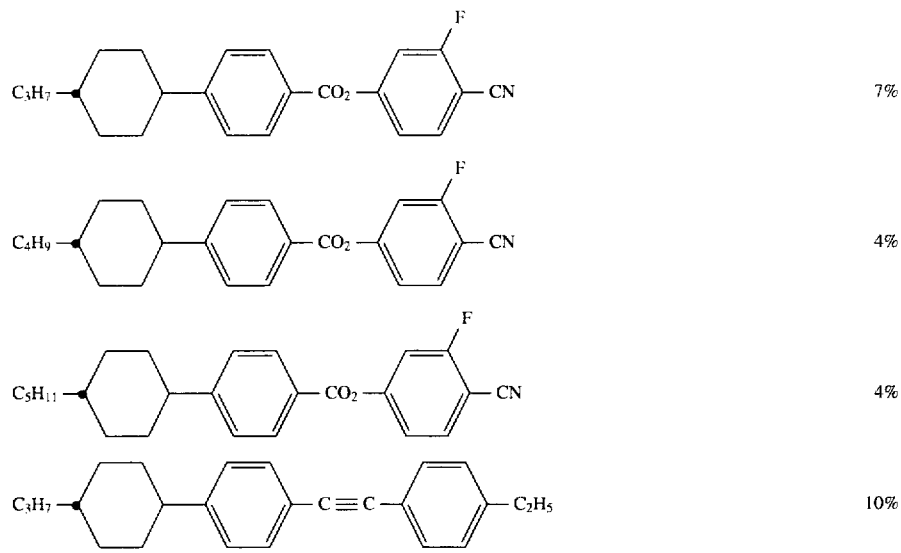

| Structure | % |
|---|---|
| C₃H₇-cyclohexyl-phenyl-CO₂-(F,CN-phenyl) | 7% |
| C₄H₉-cyclohexyl-phenyl-CO₂-(F,CN-phenyl) | 4% |
| C₅H₁₁-cyclohexyl-phenyl-CO₂-(F,CN-phenyl) | 4% |
| C₃H₇-cyclohexyl-phenyl-C≡C-phenyl-C₂H₅ | 10% |

EXAMPLE

The present invention will be described in more detail by way of Examples. In these Examples, cyclohexane ring and double bond each show trans-form. Further, Cr, S, N and Iso, respectively represent crystal, smectic phase, nematic phase and isotropic liquid, and all of the units of phase transition points refer to °C.

EXAMPLE 1

Preparation of 1-(2-(4-trifluoromethylphenyl)ethyl)-4-(4-pentylcyclohexyl)cyclohexene (wherein $R_1=C_5H_{11}-$, A=cyclohexane ring, l=0, m, n=1, B=cyclohexene ring, C=benzene ring, X, Z=hydrogen atom, Y=—$CF_3$, compound No. 3)

(First step)

A diethyl ether (250 ml) solution of 4-trifluoromethyl-bromobenzene (50 g, 0.222 mol) was dropwise added to a mixture of dry Mg (5.4 g, 0.222 mol) with diethyl ether (10 ml), followed by stirring the mixture at room temperature for 2 hours to obtain a brown, uniform solution, at one time adding to the solution, ethylene oxide (29.3 g, 0.67 mol) (heat was naturally generated and reflux occurred), stirring the mixture for one hour, feeding the reaction substance into 6N-hydrochloric acid, twice extracting with ethyl acetate (200 ml), washing the resulting organic layer with a saturated aqueous solution of sodium hydrogen carbonate, then with NaCl aqueous solution, drying over anhydrous magnesium sulfate, filtering off the anhydrous magnesium sulfate, distilling off the solvent under reduced pressure and distilling the resulting red oily substance under reduced pressure, to obtain colorless, oily 2-(4-trifluoromethylphenyl) ethylalcohol (19.0 g).

B.p.: 86° to 91° C. (4 mmHg). Yield: 45%.

(Second step)

A mixture of 2-(4-trifluoromethylphenyl) ethylalcohol (19.0 g) obtained at the first step, 47% hydrobromic acid (60 ml) and xylene (70 ml) was heated under reflux for 11 hours while removing water, followed by feeding the resulting solution into a saturated sodium hydrogen carbonate (100 ml), washing the resulting organic layer with water, drying over anhydrous magnesium sulfate, removing anhydrous magnesium sulfate, distilling off the solvent under reduced pressure and distilling the resulting residue under reduced pressure, to obtain colorless, oily 2-(4-trifluoromethylphenyl)ethyl bromide (8.43 g).

B.p.: 66.5° to 70° C. (2 mmHg). Yield: 33%.

(Third step)

A mixture of dry Mg (0.77 g, 0.032 mol), 2-(4-trifluoromethylphenyl)ethyl bromide (8.0 g, 0.032 mol) obtained at the second step and diethyl ether (40 ml) was heated at 60° C. for one hour in a sealed tube reactor to obtain a gray, uniform solution, followed by adding this solution to a diethyl ether (30 ml) solution of 4-(4-pentylcyclohexyl)cyclohexanone (7.9 g, 0.032 mol), stirring the mixture at room temperature for 3 hours, feeding the resulting reaction substance into a saturated aqueous solution of $NH_4Cl$, twice extracting with ethyl acetate (50 ml), washing the resulting organic layer, with an aqueous solution of NaCl, drying over anhydrous $MgSO_4$, removing anhydrous $MgSO_4$, distilling off the solvent under reduced pressure, to obtain pale yellow, oily 1-(2-(4-trifluoromethylphenyl)ethyl)-4-(4-pentylcyclohexyl)cyclohexanol (11.4 g), adding thereto toluene (50 ml) and Amberlyst (0.7 g), heating the mixture under reflux for one hour, while removing water formed by the reaction, allowing the resulting substance to cool, feeding it to a saturated aqueous solution of $NH_4Cl$ (100 ml), twice washing the resulting separated organic layer with water, drying over anhydrous magnesium sulfate, filtering off the anhydrous $MgSO_4$, distilling off the solvent under reduced pressure, subjecting the resulting residue to column chromatography (silica gel, eluent: heptane) and twice recrystallizing from ethanol (20 ml), to obtain 1-(2-(4-trifluoromethylphenyl)ethyl)-4-(4-pentylcyclohexyl)cyclohexene (4.1 g). Yield: 32%.

Cr-S point 70.7° C., S-N point 81.5° C., N-Iso point 88.5° C.

$^1$H-NMR ($CDCl_3$) δ (ppm) :7.38 (dd, 4H), 5.40 (brs, 1H), 2.67 (t, 2H), 2.31–0.81 (m, 30H)

MS: 406 ($M^+$)

EXAMPLE 2

Preparation of 1-(2-(4-trifluoromethyloxyphenyl)ethyl)-4-(4-pentylcyclohexyl)cyclohexene ($R_1=C_5H_{11}-$, A=cyclohexane ring, l=0, m, n=1, B=cyclohexene ring, C=benzene ring, X, Z=hydrogen atom, Y=—$OCF_3$, compound No. 9)

A mixture of 2-(4-trifluoromethyloxyphenyl)ethyl bromide (10.0 g, 0.037 mol) prepared in the same manner as in Example 1 except that 4-trifluoromethylbromobenzene was replaced by 4-trifluoromethyloxybromobenzene, with THF (50 ml), was heated at 90° C. for 40 minutes in a sealed tube reactor, to obtain a yellow, uniform solution, followed by adding this solution to a THF (40 ml) solution of 4-(4-pentylcyclohexyl)cyclohexanone (9.27 g, 0.037 mol), stirring the mixture at room temperature for 2 hours, feeding the reaction substance into a saturated aqueous solution of $NH_4Cl$, twice extracting with ethyl acetate (50 ml), washing the resulting organic layer with an aqueous solution of NaCl, drying over anhydrous $MgSO_4$, removing the anhydrous $MgSO_4$, distilling off the solvent under reduced pressure, to obtain a pale yellow, oily 1-(2-(4-trifluoromethyloxyphenyl)ethyl-4-(4-pentylcyclohexyl)cyclohexanol (19.7 g), adding thereto toluene (50 ml) and Amberlyst (0.9 g), heating the mixture under reflux for one hour, while removing formed water, allowing the resulting substance to cool, feeding it to a saturated aqueous solution of $NH_4Cl$, twice washing the separated organic layer with water, drying over anhydrous $MgSO_4$, filtering off the anhydrous $MgSO_4$, distilling off the solvent under reduced pressure, subjecting the residue to column chromatography (silica gel, eluent: heptane) and twice recrystallizing from a mixed solvent of ethanol (10 ml) with benzene (1 ml), to obtain 1-(2-(4-trifluoromethyloxyphenyl)ethyl)- 4-(4-pentylcyclohexyl)cyclohexene (1.0 g). Yield: 6%.

Cr-S point 41.0° C., S-N point 61.4° C., N-Iso 95.8° C.

$^1$H-NMR ($CDCl_3$) δ (ppm): 7.14 (s, 4H), 5.39 (brs, 1H), 2.70 (t, 2H), 2.28–0.81 (m, 30H)

MS: 422 ($M^+$)

EXAMPLE 3

Preparation of 1-(2-(4-propylcyclohexyl)ethyl)-4 -(4-trifluoromethoxyphenyl)cyclohexene ($R_1=C_3H_7-$, A=cyclohexane ring, l, m=0, n=1, C=cyclohexene ring, X, Z=H atom, Y=—$OCF_3$, compound No. 43)

(First step)

A THF (500 ml) solution of 4-trifluoromethoxybromobenzene (100 g, 0.41 mol) was dropwise added to a mixture of dry Mg (11.1 g, 0.46 mol) with THF (50 ml), followed by stirring the resulting mixture at room temperature for 2 hours, to obtain a red, uniform solution, adding thereto a THF (300 ml) solution of 1,4-cyclohexanedione monoethyleneketal (78 g, 0.5 mol) at 0° C. or lower, stirring the mixture at room temperature overnight, feeding the resulting solution into a saturated aqueous solution of $NH_4Cl$ (400 ml), extracting with toluene (500 ml), twice washing the resulting organic layer with water, drying over anhydrous $MgSO_4$, filtering off anhydrous $MgSO_4$, distilling off the solvent under reduced pressure, to obtain a red, oily (4-trifluoromethoxyphenyl)cyclohexanol- 4-one ethyleneketal (138 g), adding thereto toluene (500 ml) and Amberlyst (7 g), heating the mixture under reflux for 3 hours, while removing formed water, allowing the resulting substance to cool, feeding it into a saturated aqueous solution of $NH_4Cl$ (500 ml), twice washing the resulting separated organic layer with water, drying over anhydrous $MgSO_4$, filtering off anhydrous $MgSO_4$, distilling off the solvent under reduced pressure and subjecting the residue to column chromatography (silica gel, eluent: toluene), and recrystallizing from ethanol (30 ml), to obtain (4-trifluoromethoxyphenyl) cyclohexen-4-one ethyleneketal (43.3 g). Mp.: 53.9°–55.5° C.

(Second step)

A mixture of (4-trifluoromethoxyphenyl)cyclohexen-4-one ethyleneketal (43.3 g, 0.144 mol), ethanol (200 ml), ethyl acetate (50 ml) and Pa-C (2 g) was stirred at room temperature for 10 hours in hydrogen atmosphere (at that time, hydrogen (3.59 l) was consumed), filtering off the catalyst from the reaction solution, distilling off the solvent under reduced pressure, to obtain 4-(4-trifluoromethoxyphenyl) cyclohexanone ethyleneketal (43.5 g) (m.p. 41.2° C.), adding thereto formic acid (250 ml), heating the mixture under reflux for 2.5 hours, feeding the reaction substance into water, extracting with a mixed solvent of toluene (400 ml) with ethyl acetate (100 ml), twice washing the resulting organic layer with water, drying over anhydrous $MgSO_4$, filtering off anhydrous $MgSO_4$, distilling off the solvent under reduced pressure and subjecting the resulting residue to column chromatography (silica gel, eluent: toluene), to obtain 4-(4-trifluoromethoxyphenyl)cyclohexanone (20.7 g). Yield: 47%.

(Third step)

A THF (25 ml) solution of 2-(4-propylcyclohexyl)ethyl bromide (5.0 g, 0.021 mol) was dropwise added to a mixture of dry Mg (0.52 g, 0.021 mol) with THF (1 ml), followed by stirring the mixture at room temperature for one hour, to obtain a gray, uniform solution, dropwise adding thereto a THF (25 ml) solution of 4-(4-trifluoromethoxyphenyl)cyclohexanone (4.54 g, 0.0175 mol) obtained at the second step, at 0° C. or lower, stirring the mixture at room temperature for 3 hours, feeding the reaction substance into a saturated aqueous solution of $NH_4Cl$ (50 ml), extracting with a mixed solvent of toluene (100 ml) with ethyl acetate (50 ml), twice washing the resulting organic layer with water, drying over anhydrous $MgSO_4$, removing anhydrous $MgSO_4$, distilling off the solvent under reduced pressure, to obtain oily 1-(2-(4-propylcyclohexyl)ethyl)- 4-(4-trifluoromethoxyphenyl)cyclohexanol (7.9 g), adding thereto toluene (40 ml) and Amberlyst (3 g), heating the mixture under reflux for 4 hours, while removing formed water, allowing the resulting substance to cool, feeding it into a saturated aqueous solution of $NH_4Cl$ (100 ml), twice washing the separated organic layer with water, drying over anhydrous $MgSO_4$, filtering off anhydrous $MgSO_4$, distilling off the solvent under reduced pressure, subjecting the resulting residue to column chromatography (silica gel, eluent: heptane) and twice recrystallizing from ethanol (4 ml), to obtain 1-(2-(4-propylcyclohexyl)ethyl)- 4-(4-trifluoromethoxyphenyl)cyclohexene (1.26 g). Yield: 18%.

Cr-N point 51.3° C. N-Iso point 62.2° C.

$^1$H-NMR ($CDCl_3$) δ (ppm): 7.30–7.06 (m, 4H), 5.48 (brs, 1H), 2.73 (m, 1H), 2.25–0.79 (m, 27H), MS: 394 ($M^+$)

According to Examples 1 to 3 and the detailed description of the invention, the compounds mentioned below can be prepared. In addition, in the respective compounds, compound No. 3, compound No. 9 and compound No. 43 are together shown. Further, the respective compounds are indicated by parameters.

| No. | $R_1$ | $-A+CH_2CH_2)_l(B)_m-CH_2CH_2+C)_n$ | l | m | n | X | Z | Y | |
|---|---|---|---|---|---|---|---|---|---|
| 1 | $C_3H_7$ | 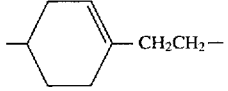 | 0 | 0 | 0 | F | F | $CF_3$ | |
| 2 | $C_3H_7$ | 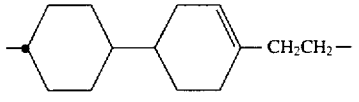 | 0 | 1 | 0 | H | H | $CF_3$ | |
| 3 | $C_5H_{11}$ | 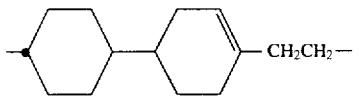 | 0 | 1 | 0 | H | H | $CF_3$ | Cr 70.7 S 81.5 N 88.5 I |
| 4 | $C_3H_7CH=CH$ | 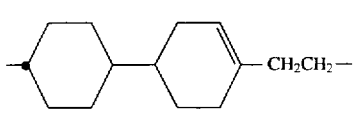 | 0 | 1 | 0 | H | H | $CF_3$ | |
| 5 | $C_3H_7$ | 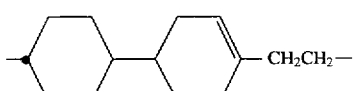 | 0 | 1 | 0 | F | H | $CF_3$ | |
| 6 | $C_3H_7$ | 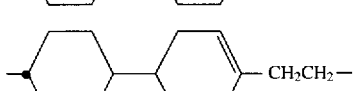 | 0 | 1 | 0 | F | F | $CF_3$ | |
| 7 | $C_5H_{11}$ | 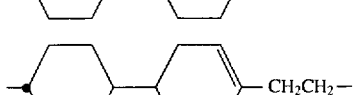 | 0 | 1 | 0 | F | F | $CF_3$ | |
| 8 | $FCH_2CH_2$ | 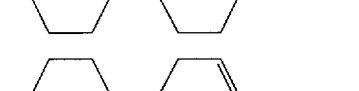 | 0 | 1 | 0 | H | H | $OCF_3$ | S 33.7 N 54.7 I |
| 9 | $C_5H_{11}$ | 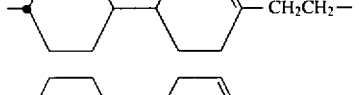 | 0 | 1 | 0 | H | H | $OCF_3$ | Cr 41.0 S 61.4 N 95.8 I |
| 10 | $CH_3CH=CHC_2H_4$ | 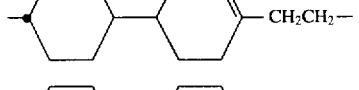 | 0 | 1 | 0 | H | H | $OCF_3$ | |
| 11 | $C_3H_7$ | 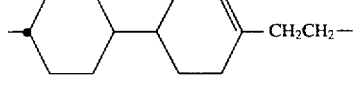 | 0 | 1 | 0 | F | H | $OCF_3$ | |
| 12 | $C_3H_7$ | 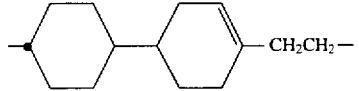 | 0 | 1 | 0 | F | F | $OCF_3$ | |
| 13 | $C_3H_7$ | 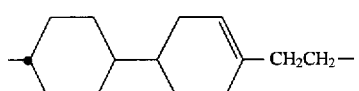 | 0 | 1 | 0 | F | Cl | $OCF_3$ | |
| 14 | $C_3H_7$ | 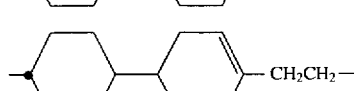 | 0 | 1 | 0 | H | H | $OC_2H_5$ | |
| 15 | $C_3H_7$ | 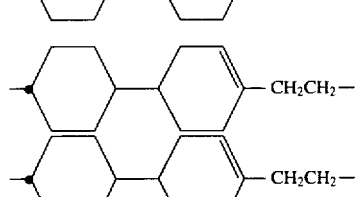 | 0 | 1 | 0 | F | H | $OCF_2H$ | |

-continued

| No. | R₁ | −A−(CH₂CH₂)ₗ(B)ₘ−CH₂CH₂−(C)ₙ− | l | m | n | X | Z | Y |
|---|---|---|---|---|---|---|---|---|
| 16 | C₃H₇ | ⬡−⬡−CH₂CH₂− | 0 | 1 | 0 | F | H | OCF₂CF₂H |
| 17 | C₃H₇ | ⬡−⬡−CH₂CH₂− | 0 | 1 | 0 | H | H | OCF₂CFHCF₃ |
| 18 | C₃H₇ | ⬡−⬡−CH₂CH₂− | 0 | 1 | 0 | F | H | OCF₂CFHCF₃ |
| 19 | C₃H₇ | ⬡−⬡−CH₂CH₂− | 0 | 1 | 0 | F | F | OCF₂CFHCF₃ |
| 20 | C₃H₇ | ⬡−⬡−CH₂CH₂− | 0 | 1 | 0 | H | H | CF₃ |
| 21 | C₃H₇ | ⬡−CH₂CH₂−⬡−CH₂CH₂− | 1 | 1 | 0 | H | H | CF₃ |
| 22 | C₅H₁₁ | ⬡−CH₂CH₂−⬡−CH₂CH₂− | 1 | 1 | 0 | F | H | CF₃ |
| 23 | C₅H₁₁ | ⬡−CH₂CH₂−⬡−CH₂CH₂− | 1 | 1 | 0 | F | F | CF₃ |
| 24 | C₃H₇ | ⬡−CH₂CH₂−⬡−CH₂CH₂− | 1 | 1 | 0 | F | H | OCF₃ |
| 25 | C₃H₇ | ⬡−CH₂CH₂−⬡−CH₂CH₂− | 1 | 1 | 0 | F | H | OCF₂CF₂H |
| 26 | C₃H₇ | ⬡−CH₂CH₂−⬡−CH₂CH₂− | 1 | 1 | 0 | F | H | OCF₂CFHCF₃ |
| 27 | C₃H₇ | ⬡−CH₂CH₂−⬡− | 0 | 0 | 1 | H | H | CF₃ |
| 28 | C₃H₇ | ⬡−CH₂CH₂−⬡− | 0 | 0 | 1 | F | F | CF₃ |
| 29 | C₃H₇ | ⬡−CH₂CH₂−⬡− | 0 | 0 | 1 | H | H | OCF₃ |
| 30 | C₃H₇ | ⬡−CH₂CH₂−⬡− | 0 | 0 | 1 | F | H | OCF₃ |

-continued
| No. | R₁ | $-A+CH_2CH_2)_l(B)_m-CH_2CH_2+C)_n$ | l | m | n | X | Z | Y | |
|---|---|---|---|---|---|---|---|---|---|
| 31 | $C_3H_7$ | 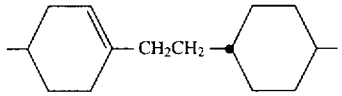 | 0 | 0 | 1 | F | Cl | $OCF_3$ | |
| 32 | $C_3H_7$ | 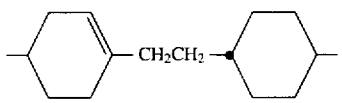 | 0 | 0 | 1 | H | H | $OCF_2CF_2H$ | |
| 33 | $C_3H_7$ | 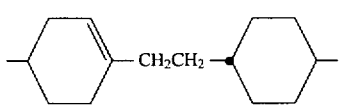 | 0 | 0 | 1 | H | H | $OCF_2CFHCF_3$ | |
| 34 | $C_3H_7$ | 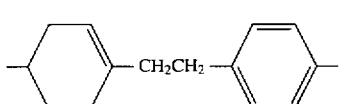 | 0 | 0 | 1 | H | H | $CF_3$ | |
| 35 | $C_5H_{11}$ | 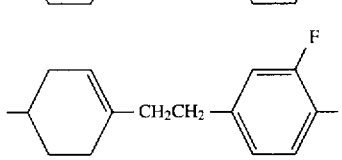 | 0 | 0 | 1 | F | H | $CF_3$ | |
| 36 | $C_3H_7$ | 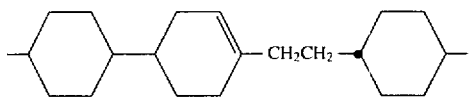 | 0 | 1 | 1 | F | H | $OCF_3$ | |
| 37 | $C_3H_7$ | 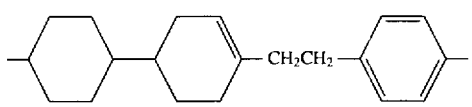 | 0 | 1 | 1 | F | F | $CF_3$ | |
| 38 | $C_3H_7$ | 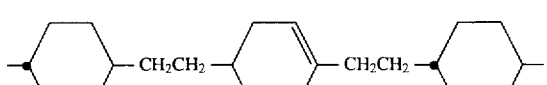 | 1 | 1 | 1 | H | H | $CF_3$ | |
| 39 | $C_5H_{11}$ | 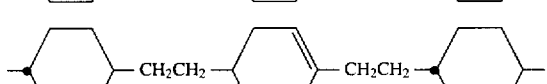 | 1 | 1 | 1 | F | Cl | $OCF_3$ | |
| 40 | $C_3H_7$ | 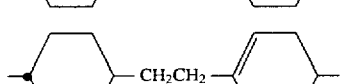 | 0 | 0 | 1 | H | H | $CF_3$ | Cr 108.0 I |
| 41 | $C_5H_{11}$ | 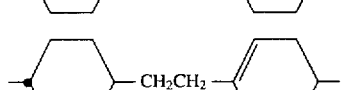 | 0 | 0 | 1 | F | H | $CF_3$ | |
| 42 | $C_3H_7$ |  | 0 | 0 | 1 | F | F | $CF_3$ | |
| 43 | $C_3H_7$ |  | 0 | 0 | 1 | H | H | $OCF_3$ | Cr 51.3 N 62.2 I |
| 44 | $C_3H_7$ |  | 0 | 0 | 1 | F | H | $OCF_3$ | |

-continued

| No. | $R_1$ | $-A\!-\!(CH_2CH_2)_l\!-\!(B)_m\!-\!CH_2CH_2\!-\!(C)_n\!-$ | l | m | n | X | Z | Y | |
|---|---|---|---|---|---|---|---|---|---|
| 45 | $C_3H_7$ | Cy–CH$_2$CH$_2$–Cy= | 0 | 0 | 1 | F | F | $OCF_3$ | |
| 46 | $C_3H_7$ | Cy–CH$_2$CH$_2$–Cy= | 0 | 0 | 1 | H | H | $OC_2F_5$ | |
| 47 | $C_3H_7$ | Cy–CH$_2$CH$_2$–Cy= | 0 | 0 | 1 | F | H | $OCF_2CF_2H$ | |
| 48 | $C_5H_{11}$ | Cy–CH$_2$CH$_2$–Cy= | 0 | 0 | 1 | F | H | $OCF_2CF_2H$ | |
| 49 | $C_3H_7$ | Cy–CH$_2$CH$_2$–Cy= | 0 | 0 | 1 | F | F | $OCF_2CF_2H$ | |
| 50 | $C_5H_{11}$ | Cy–CH$_2$CH$_2$–Cy= | 0 | 0 | 1 | F | F | $OCF_2CFHCF_3$ | |
| 51 | $C_5H_{11}$ | Cy–CH$_2$CH$_2$–Cy= | 0 | 0 | 1 | H | H | $OC_4H_9$ | |
| 52 | $C_3H_7$ | Ph–CH$_2$CH$_2$–Cy= | 0 | 0 | 1 | H | H | $CF_3$ | |
| 53 | $C_3H_7$ | Ph(F)–CH$_2$CH$_2$–Cy= | 0 | 0 | 1 | H | H | $CF_3$ | |
| 54 | $C_3H_7$ | Ph–CH$_2$CH$_2$–Cy= | 0 | 0 | 1 | H | H | $OCF_3$ | |
| 55 | $C_5H_{11}$ | Ph–CH$_2$CH$_2$–Cy= | 0 | 0 | 1 | H | H | $OCF_3$ | |
| 56 | $CH_3O$ | Ph–CH$_2$CH$_2$–Cy= | 0 | 0 | 1 | H | H | $OCF_3$ | Cr 81.3 I |
| 57 | $C_3H_7O$ | Ph–CH$_2$CH$_2$–Cy= | 0 | 0 | 1 | H | H | $OCF_3$ | |
| 58 | $C_3H_7$ | Ph–CH$_2$CH$_2$–Cy= | 0 | 0 | 1 | F | F | $OCF_2CF_2H$ | |

-continued

| No. | $R_1$ | $-A-(CH_2CH_2)_l-(B)_m-CH_2CH_2-(C)_n-$ | l | m | n | X | Z | Y | |
|---|---|---|---|---|---|---|---|---|---|
| 59 | $C_5H_{11}$ | Ph-CH₂CH₂-Cy | 0 | 0 | 1 | F | F | $OCF_2CFHCF_3$ | |
| 60 | $C_3H_7$ | Cy-Cy-CH₂CH₂-Cy | 0 | 1 | 1 | F | F | $CF_3$ | |
| 61 | $C_5H_{11}$ | Cy-Cy-CH₂CH₂-Cy | 0 | 1 | 1 | H | H | $OCF_3$ | S 188.6 N 211.5 I |
| 62 | $C_5H_{11}$ | Cy-Cy-CH₂CH₂-Cy | 0 | 1 | 1 | F | H | $OCF_3$ | |
| 63 | $C_3H_7$ | Cy-Ph-CH₂CH₂-Cy | 0 | 1 | 1 | F | F | $CF_3$ | |
| 64 | $C_3H_7$ | Cy-Ph(F,F)-CH₂CH₂-Cy | 0 | 1 | 1 | F | F | $CF_3$ | |
| 65 | $C_3H_7$ | Ph-Cy-CH₂CH₂-Cy | 0 | 1 | 1 | F | H | $CF_3$ | |
| 66 | $C_3H_7$ | Cy-CH₂CH₂-Cy-CH₂CH₂-Cy | 1 | 1 | 1 | F | H | $CF_3$ | |
| 67 | $C_3H_7$ | Cy-CH₂CH₂-Cy-CH₂CH₂-Cy | 1 | 1 | 1 | H | H | $CF_3$ | |
| 68 | $C_5H_{11}$ | Ph-CH₂CH₂-Cy-CH₂CH₂-Cy | 1 | 1 | 1 | H | H | $OCF_3$ | |
| 69 | $C_5H_{11}$ | Ph-CH₂CH₂-Cy-CH₂CH₂-Cy | 1 | 1 | 1 | F | H | $OCF_3$ | |

EXAMPLE 4

(Use example 1)

A liquid crystal composition $A_1$ consisting of the following composition was prepared as a mother liquid crystal:

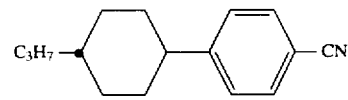  24%

-continued

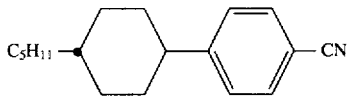  36%

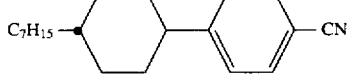  25%

   15%

The values of physical properties of this composition $A_1$ were as follows:

Clearing point: 100.2° C. $\Delta n$: 0.093, ds: 5.1, viscosity $\eta$ at 20° C.: 24.5 mPas, and threshold voltage in a cell thickness of 8.8 µm: 2.15 V.

Next, to this composition $A_1$ (80%) was added 1-(2-(4-propylcyclohexyl)ethyl)-4-(4-trifluoromethoxyphenyl)cyclohexene (Compound No. 43 obtained in Example 3) (20%), to prepare a composition $B_1$, and its values of physical properties were sought, and they were as follows and the values within parentheses were calculated extrapolated values, and this applies to Examples mentioned below:

Clearing point: 92.4 (61.2)° C., $\Delta n$: 0.092 (0.088), $\Delta\epsilon$: 4.9 (4.1), viscosity $\eta$ at 20° C.: 23.9 (18.3) mPas, and threshold voltage in a cell thickness of 8.7 µm: 2.27 V.

EXAMPLE 5

(Use example 2)

A liquid crystal composition A2 consisting of the following composition was prepared as a mother liquid crystal:

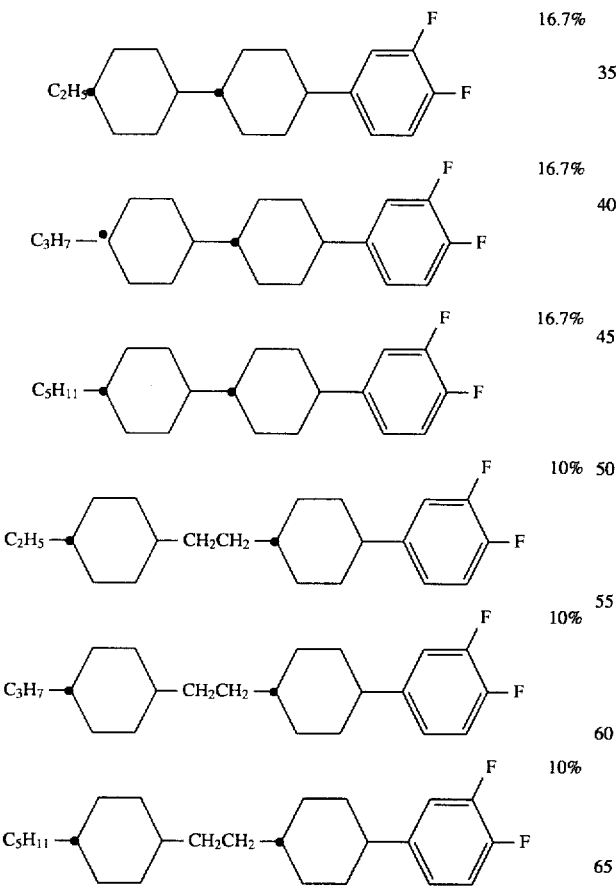

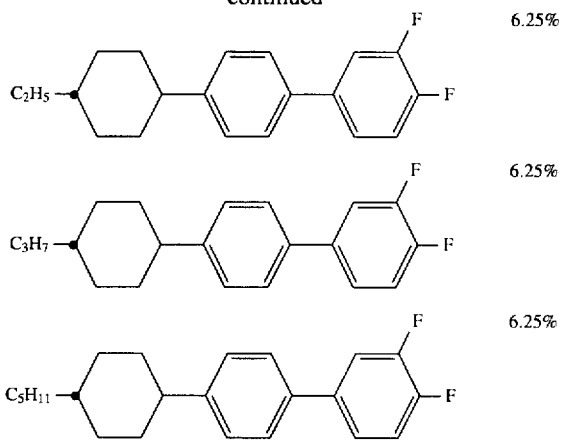

The values of physical properties of this composition $A_2$ were as follows:

Clearing point: 72.4° C., $\Delta n$: 0.137, $\Delta\epsilon$: 11.0, viscosity $\eta$ at 20° C.: 27.0 mPas, and threshold voltage in a cell thickness of 9.0 µm: 1.78 V.

Next, to this composition A2 (85%) was added 1-2-(4-trifluoromethylphenyl)ethyl-4-(4-pentylcyclohexyl)cyclohexene (compound No. 3 obtained in Example 1) (15%), to prepare a composition $B_2$, and its values of physical properties were sought. The results were as follows:

Clearing point: 72.1 (70.4)° C., $\Delta n$: 0.130 (0.090), $\Delta\epsilon$: 10.6 (8.3), viscosity $\eta$ at 20° C.: 26.5 (23.7) mPas; and threshold voltage in a cell thickness of 8.8 µm: 1.75 V.

EXAMPLE 6

(Use example 3)

To the composition A2 used in Example 5 (85%) was added 1-(2-(4-trifluoromethyloxyphenyl)ethyl)-4-(4-pentylcyclohexyl)cyclohexene (compound No. 9 obtained in Example 2) (15%), to prepare a composition $B_3$, and its values of physical properties were sought. The results were as follows:

Clearing point: 71.3 (65.1) ° C., $\Delta n$: 0.123 (0.044), $\Delta\epsilon$: 10.0 (4.3), viscosity $\eta$ at 20° C.: 38.3 (102.3) mPas, and threshold voltage in a cell thickness of 8.7 µm: 1.68 V.

EXAMPLE 7

(Use example 4)

To the above composition $A_2$ (85%) was added 1-(2-(4-propylcyclohexyl)ethyl)-4-(4-trifluoromethoxyphenyl)cyclohexene (compound No. 43) (15%), to prepare a composition $B_4$, and its values of physical properties were sought. The results were as follows:

Clearing point: 69.2 (51.1)° C., $\Delta n$: 0.128 (0.077), $\Delta\epsilon$: 10.2 (5.7), viscosity $\eta$ at 20° C.: 24.7 (11.7) mPas, and threshold voltage in a cell thickness of 8.7 µm: 1.76 V.

EXAMPLE 8

(Use example 5)

To the above composition $A_2$ (85%) was added 1-(2-(4-methyloxyphenyl)ethyl)-4-(4-trifluoromethoxyphenyl)cyclohexene (compound No. 56) (15%), to prepare a composition $B_5$, and its values of physical properties were sought. The results were as follows:

Clearing point: 68.0 (43.1)° C., Δn: 0.135 (0.124), Δε: 10.9 (10.3), viscosity η at 20° C.: 29.2 (41.7) mPas, and threshold voltage in a cell thickness of 8.7 μm: 1.62 V.

EXAMPLE 9

(Use example 6)

To the above composition $A_2$ (85%) was added 1-(2—(4 -(4-pentylcyclohexyl)cyclohexyl)ethyl)-4-(4-trifluoromethoxyphenyl)cyclohexene (compound No. 61) (15%), to prepare a composition $B_6$, and its values of physical properties were sought. The results were as follows:

Clearing point: 69.0 (163.6)° C., Δn: 0.119 (0.119), Δε: 10.3 (8.0) and threshold voltage in a cell thickness of 8.9 μm: 1.74 V.

EXAMPLE 10

(Use example 7)

To the above composition $A_1$ used in Example 4 (80%) was mixed 1-(2-(4-propylcyclohexyl)ethyl-4-(4 -trifluoromethoxyphenyl)cyclohexene (compound No. 43) (20%), to prepare a composition BT. The voltage-holding ratios of this composition $B_7$ at the respective temperatures were measured. The results were shown in the following Table.

examples 2, 3 or 4 of the below Table were respectively added in place of the compound No. 3, and their values of physical properties (extrapolated values) were sought in the same manner as the above.

| Added compound | 25 | 45 | 65 | 85 | 90 | (°C.) |
|---|---|---|---|---|---|---|
| Example 10 | 98.0 | 97.5 | 96.8 | 95.7 | 94.7 | (%) |
| 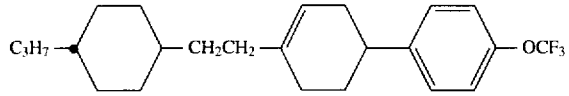 | | | | | | |
| Comparative example 1 | 97.9 | 97.9 | 96.9 | 94.1 | 93.4 | (%) |
| 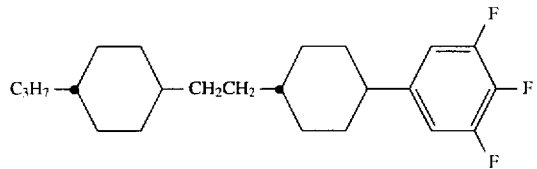 | | | | | | |

In addition, in this table, a case where 1,2,3 -trifluoro-5-(4-(2-(4-propylcyclohexyl)ethyl)cyclohexyl)benzene as Comparative example 1 was mixed in place of (43), is shown together.

Comparative Examples 2 to 4

Compositions were prepared in the same manner as in Example 5 except that compounds shown in Comparative

| | N-I (°C.) | Δε | Δn | η (cp) | $V_{10}$ (V) |
|---|---|---|---|---|---|
| Example 5 | 70.4 | 8.3 | 0.090 | 23.7 | 1.75 |
| 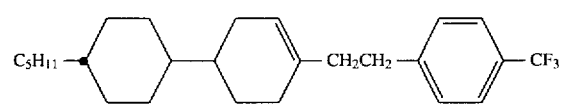 | | | | | |
| Comparative example 2 | 70.4 | 6.3 | 0.077 | 42.3 | 1.67 |

|   | N-I (°C.) | Δε | Δn | η (cp) | V₁₀ (V) |
|---|---|---|---|---|---|

C₅H₁₁—⟨H⟩—⟨H⟩—CH₂CH₂—⟨Ph(F,F)⟩

Comparative example 3 | 97.7 | 11.0 | 0.104 | 28.3 | 1.85

C₃H₇—⟨H⟩—⟨H⟩—⟨Ph⟩—CF₃

Comparative example 4 | 103.0 | 8.3 | 0.090 | 21.0 | 1.78

C₃H₇—⟨H⟩—⟨H⟩—⟨Ph(F,F)⟩

In comparison of Example 5 with Comparative example 2, the two are same in the aspect of their N-I points, but the viscosity of the former is lower, and the $\Delta n$, $\Delta \varepsilon$ and threshold voltage $V_{10}$ of the latter are lower. In other words, it is shown that the former can inhibit the increase in the viscosity, while preferably retaining the characteristics for TFT.

This consists in a reverse relationship to a fact taught from comparison of a known compound shown in example 3, having the same $CF_3$ group on benzene ring as that of compound used in Comparative Example 5, with a known compound shown in Comparative example 4, having the same two fluorine atom as those in Comparative example 2, that is, a fact that as to viscosity, the compound of Comparative example 3 having $CF_3$ group is higher. Namely, entirely unanticipated results were obtained.

Such results obtained in the present invention are considered to be due to the fact that the compound of the present invention contains a cyclohexene ring in its molecule and the interaction of the ring with various substituents is preferably effected.

EXAMPLE 11

(Use example 8)

A liquid crystal composition B8 was prepared, which consisted of

| | |
|---|---|
| 4-(4-pentylcyclohexyl)-1-(2-(4-trifluoromethyl-phenyl)ethyl)cyclohexene (compound No. 3) | 5% |
| 4-(4-pentylcyclohexyl)-1-(2-(4-trifluoromethoxy-phenyl)ethyl)cyclohexene (compound No. 9) | 3% |
| 4-(4'-ethylbicyclohexyl)-1,2-difluorobenzene | 12% |
| 4-(4'-propylbicyclohexyl)-1,2-difluorobenzene | 12% |
| 4-(4'-pentylbicyclohexyl)-1,2-difluorobenzene | 12% |
| 4-(4'-propylbicyclohexyl)-1,2,6-trifluorobenzene | 6% |
| 4-(4'-pentylbicyclohexyl)-1,2,6-trifluorobenzene | 6% |
| 4-(4-(2-(4-propylcyclohexyl)ethyl)cyclohexyl)-1,2,6-trifluorobenzene | 5% |
| 4-(4-(2-(4-pentylcyclohexyl)ethyl)cyclohexyl)-1,2,6-trifluorobenzene | 5% |
| 4-(2-(4'-propylbicyclohexyl)ethyl)-1,2,6-trifluorobenzene | 5% |
| 4-(2-(4'-pentylbicyclohexyl)ethyl)-1,2,6-trifluorobenzene | 5% |
| 4-(4-heptylcyclohexyl)-1,2,6-trifluorobenzene | 9% |
| 4'-(2-(4-propylcyclohexyl)ethyl)-3,4,5-trifluoro-biphenyl | 8% |
| 4'-(2-(4-pentylcyclohexyl)ethyl)-3,4,5-trifluoro-biphenyl | 8%, | and its values of physical properties were measured. The results were as follows:

Clearing point: 75.4° C., $\Delta n$: 0.0809, $\Delta \varepsilon$: 6.9, viscosity $\eta$ at 20° C.: 23.4 mPas; and threshold voltage in a cell thickness of 8.9 μm: 1.65 V

EXAMPLE 12

(Use example 9)

A liquid crystal composition B9 was prepared, which consisted of

| | |
|---|---|
| 4-(4-pentylcyclohexyl)-1-(2-(4-trifluoromethyl-phenyl)ethyl)cyclohexene (compound No. 3) | 5% |
| 4-(4-trifluoromethylphenyl)-1-(2-(4-propylcyclo-phexyl)ethyl)cyclohexene (compound No. 40) | 5% |
| 4-(4-heptylcyclohexyl)-1,2-difluorobenzene | 5% |
| 4-(2-(4-pentylcyclohexyl)ethyl)-1,2-difluoro-benzene | 10% |
| 4-(4-(2-(4-ethylcyclohexyl)ethyl)cyclohexyl)-1,2-difluorobenzene | 12% |
| 4-(4-(2-(4-propylcyclohexyl)ethyl)cyclohexyl)-1,2-difluorobenzene | 6% |
| 4-(4-(2-(4-pentylcyclohexyl)ethyl)cyclohexyl)-1,2-difluorobenzene | 12% |
| 4-(4-pentylcyclohexyl)-1-chlorobenzene | 5% |
| 4-(4-heptylcyclohexyl)-1-chlorobenzene | 5% |
| 4-(4-(2-(4-propylcyclohexyl)ethyl)cyclohexyl)-2-fluoro-1-chlorobenzene | 5% |
| 4-(4'-propylcyclohexyl)-1-fluorobenzene | 5% |
| 4'-(4-propylcyclohexyl)-4-fluorobiphenyl | 5% |
| 4'-(4-propylcyclohexyl)-3,4,5-trifluorobiphenyl and | 7% |
| 4'-(4-pentylcyclohexyl)-3,4,5-trifluorobiphenyl | 8% |

Its values of physical properties were measured. The results are as follows:

Clearing point: 62.1° C.,

Δn: 0.0847; Δε: 4.8, viscosity η at 20 ° C.: 20.1 mPas, and threshold voltage in a cell thickness of 8.7 μm: 1.92 V.

EXAMPLE 13

(Use example 10)

A liquid crystal composition B10 was prepared, which consisted of

| | |
|---|---|
| 4-(4-trifluoromethoxyphenyl)-1-(2-(4'-pentylbi-cyclohexyl)ethyl)cyclohexene (compound No. 61) | 5% |
| 4-(4-pentylcyclohexyl)-1-(2-(4-trifluoromethyl-phenyl)ethyl)cyclohexene (compound No. 3) | 5% |
| 4-(4-trifluoromethylphenyl)-1-(2-(4-propylcyclo-hexyl)ethyl)cyclohexene (compound No. 40) | 15% |
| 4-(4'-ethylbicyclohexyl)-1,2-difluorobenzene | 7% |
| 4-(4'-propylbicyclohexyl)-1,2-difluorobenzene | 7% |
| 4-(4'-pentylbicyclohexyl)-1,2-difluorobenzene | 7% |
| 4'-(4-ethylcyclohexyl)-3,4-difluorobiphenyl | 5% |
| 4'-(4-propylcyclohexyl)-3,4-difluorobiphenyl | 5% |
| 4'-(4-pentylcyclohexyl)-3,4-difluorobiphenyl | 10% |
| 4'-(4-propylcyclohexyl)-3,4,5-trifluorobiphenyl | 5% |
| 4'-(4-pentylcyclohexyl)-3,4,5-trifluorobiphenyl | 4% |
| 4'-(2-(4-propylcyclohexyl)ethyl)-3,4,5-trifluoro-biphenyl | 5% |
| 4'-(2-(4-pentylcyclohexyl)ethyl)-3,4,5-trifluoro-biphenyl | 5% |
| 4-(4-heptylcyclohexyl)-1-chlorobenzene | 5% |
| 4-(4'-propylbicyclohexyl)-1-chlorobenzene | 5% |
| 4-(4'-pentylbicyclohexyl)-1-chlorobenzene | 5% |

Its values of physical properties were measured. The results were as follows:

Clearing point: 90.5° C.,

Δn: 0.1085, Δε: 6.4, viscosity η at 20 ° C.: 25.9 mPas, and threshold voltage in a cell thickness of 8.7 μm: 2.21 V.

EXAMPLE 14

(Use example 11)

A liquid crystal composition B11 was prepared, which consisted of

| | |
|---|---|
| 4-(4-pentylcyclohexyl)-1-(2-(4-trifluoromethyl-phenyl)ethyl)cyclohexene (compound No. 3) | 5% |
| 4-(4-trifluoromethylphenyl)-1-(2-(4-propylcyclo-hexyl)ethyl)cyclohexene (compound No. 40) | 10% |
| 4-(4'-ethylcyclohexyl)-1,2-difluorobenzene | 7% |
| 4-(4'-propylcyclohexyl)-1,2-difluorobenzene | 7% |
| 4-(4'-pentylcyclohexyl)-1,2-difluorobenzene | 7% |
| 4-(4-(2-(4-ethylcyclohexyl)ethyl)cyclohexyl)-1,2-difluorobenzene | 10% |
| 4-(4-(2-(4-propylcyclohexyl)ethyl)cyclohexyl)-1,2-difluorobenzene | 5% |
| 4-(4-(2-(4-pentylcyclohexyl)ethyl)cyclohexyl)-1,2-difluorobenzene | 10% |
| 4-fluorophenyl=4-pentylcyclohexanecarboxylate | 5% |
| 4-fluorophenyl=4-heptylcyclohexanecarboxylate | 4% |
| 4-(4'-propylbicyclohexyl)-1,2,6-trifluorobenzene | 5% |
| 4-(4'-pentylbicyclohexyl)-1,2,6-trifluorobenzene | 5% |
| 4'-(4-propylcyclohexyl)-3,4,5-trifluorobiphenyl | 5% |
| 4'-(4-pentylcyclohexyl)-3,4,5-trifluorobiphenyl | 5% |
| 4-(4'-propylbicyclohexyl)-1-methylbenzene | 5% |
| 4-(4'-propylbicyclohexyl)-1-propylbenzene | 5% |

Its values of physical properties were measured. The results were as follows:

Clearing point: 88.2° C.,

Δn: 0.0833, Δε: 5.3, viscosity η at 20° C.: 24.3 mPas, and threshold voltage in a cell thickness of 8.7 μm: 2.20 V.

EXAMPLE 15

(Use example 12)

A liquid crystal composition B12 was prepared, which consisted of

| | |
|---|---|
| 4-(4-pentylcyclohexyl)-1-(2-(4-trifluoromethoxy-phenyl)ethyl)cyclohexene (compound No. 9) | 8% |
| 4-(4-trifluoromethylphenyl)-1-(2-(4-propylcyclo-hexyl)ethyl)cyclohexene (compound No. 40) | 12% |
| 4-(4-pentylcyclohexyl)-1-(2-(4-trifluoromethyl-phenyl)ethyl)cyclohexene (compound No. 3) | 5% |
| 4-(4-pentylcyclohexyl)-1-chlorobenzene | 5% |
| 4-(4-heptylcyclohexyl)-1-chlorobenzene | 5% |
| 4-(4'-ethylbicyclohexyl)-1-chlorobenzene | 8% |
| 4-(4'-propylbicyclohexyl)-1-chlorobenzene | 8% |
| 4-(4'-pentylbicyclohexyl)-1-chlorobenzene | 8% |
| 4-(4'-propylbicyclohexyl)-1,2,6-trifluorobenzene | 5% |
| 4-(4'-pentylbicyclohexyl)-1,2,6-trifluorobenzene | 5% |
| 4'-(4-propylcyclohexyl)-3,4,5-trifluorophenyl-benzene | 5% |
| 4'-(4-pentylcyclohexyl)-3,4,5-trifluorophenyl-benzene | 5% |
| 4-(4-(2-(4-ethylcyclohexyl)ethyl)cyclohexyl)-2-fluoro-1-chlorobenzene | 7% |
| 4-(4-(2-(4-propylcyclohexyl)ethyl)cyclohexyl)-2-fluoro-1-chlorobenzene | 7% |
| 4-(4-(2-(4-pentylcyclohexyl)ethyl)cyclohexyl)-2-fluoro-1-chlorobenzene | 7% |

Its values of physical properties were measured. The results were as follows:

Clearing point: 97.7° C.

Δn: 0.0991, Δε: 5.6, viscosity η at 20° C.: 32.2 mPas, and threshold voltage in a cell thickness of 8.7 μm: 2.44 V.

EXAMPLE 16

(Use example 13)

A liquid crystal composition B13 was prepared, which consisted of

| | |
|---|---|
| 4-(4-pentylcyclohexyl)-1-(2-(4-trifluoromethyl-phenyl)ethyl)cyclohexene (compound No. 3) | 5% |
| 4-(4-trifluoromethylphenyl)-1-(2-(4-propylcyclo-hexyl)ethyl)cyclohexene (compound No. 40) | 10% |
| 4-(4-propylcyclohexyl)-2-fluorobenzonitrile | 5% |
| 4-(4-ethylcyclohexyl)benzonitrile | 10% |
| 4-(4-propylcyclohexyl)benzonitrile | 10% |
| 4-(2-(2-fluoro-4-(4-propylcyclohexyl)phenyl)-ethynyl)-1-ethylbenzene | 5% |
| 4-(2-(2-fluoro-4-(4-propylcyclohexyl)phenyl)-ethynyl)-1-propylbenzene | 5% |
| 4-(4'-ethylbicyclohexyl)benzonitrile | 5% |
| 4-(4'-propylbicyclohexyl)benzonitrile | 5% |
| 4-fluorophenyl=4'-propylbicyclohexanecarboxylate | 5% |
| 4-fluorophenyl=4'-pentylbicyclohexanecarboxylate | 5% |
| 4-(4'-propylbicyclohexyl)-1-methoxybenzene | 5% |
| 4-(4'-propylbicyclohexyl)-1-methylbenzene | 5% |
| 4-(4'-propylbicyclohexyl)-1-propylbenzene | 5% |
| 4-(4'-ethylbicyclohexyl)-1,2-difluorobenzene | 5% |
| 4-(4'-propylbicyclohexyl)-1,2-difluorobenzene | 5% |
| 4-(4'-pentylbicyclohexyl)-1,2-difluorobenzene | 5%. |

Its values of physical properties were measured. The results were as follows:

Clearing point: 111.6° C.,

Δn: 0.1196, Δε: 7.7, viscosity η at 20° C.: 27.8 mPas, and threhsold voltage in a cell thickness of 8.7 μm: 20.08 V.

EXAMPLE 17

(Use example 14)

A liquid crystal composition $B_{14}$ was prepared, which consisted of

| | |
|---|---|
| 4-(4-pentylcyclohexyl)-1-(2-(4-trifluoromethyl-phenyl)ethyl)cyclohexene (compound No. 3) | 7% |
| 4-(4-trifluoromethylphenyl)-1-(2-(4-propylcyclo-hexyl)ethyl)cyclohexene (compound No. 40) | 8% |
| 4-(4-(3-butenyl)cyclohexyl)benzonitrile | 10% |
| 4-(4-(3-pentenyl)cyclohexyl)benzonitrile | 10% |
| 4-(4-propylcyclohexyl)benzonitrile | 9% |
| 4-(4-methoxymethylcyclohexyl)benzonitrile | 3% |
| 2-(3,4-difluorophenyl)-5-propylpyrimidine | 3% |
| 4'-methoxymethyl-4-propylcyclohexane | 7% |
| 4'-propyl-4-butylbicyclohexane | 8% |
| 4-(2-(4-ethylphenyl)ethynyl)-1-methoxybenzene | 3% |
| 4-(2-(4-propylphenyl)ethynyl)-1-methoxybenzene | 3% |
| 4-(2-(4-butylphenyl)ethynyl)-1-methoxybenzene | 3% |
| 4-(2-(4-butylphenyl)ethynyl)-1-ethoxybenzene | 3% |
| 4-(2-(4-pentylphenyl)ethynyl)-1-methoxybenzene | 3% |
| 4-(4'-propylbicyclohexyl)-1-methoxybenzene | 5% |
| 4-(4'-propylbicyclohexyl)-1-fluorobenzene | 5% |
| 4-(4'-propylbicyclohexyl)-1-methylbenzene | 5% |
| 4-(4'-propylbicyclohexyl)-1-propylbenzene | 5% |

Its values of physical properties were measured. The results were as follows:

Clearing point: 71.3° C..

Δn: 0.1256, Δε: 6.4, viscosity η at 20° C.: 16.8 mPas, and threhsold voltage in a cell thickness of 8.7 μm: 1.98 V.

EXAMPLE 18

(Use example 15)

A liquid crystal composition B15 was prepared, which consisted of

| | |
|---|---|
| 4-(4-pentylcyclohexyl)-1-(2-(4-trifluoromethyl-phenyl)ethyl)cyclohexene (compound No. 3) | 3% |
| 4-(4-(2-fluoroethyl)cyclohexyl)-1-(2-(4-trifluoro-methoxyphenyl)ethyl)cyclohexene (compound No. 8) | 5% |
| 4-(4'-ethylbicyclohexyl)-1,2-difluorobenzene | 12% |
| 4-(4'-propylbicyclohexyl)-1,2-difluorobenzene | 12% |
| 4-(4'-pentylbicyclohexyl)-1,2-difluorobenzene | 12% |
| 4-(4'-propylbicyclohexyl)-1,2,6-trifluorobenzene | 6% |
| 4-(4'-pentylbicyclohexyl)-1,2,6-trifluorobenzene | 6% |
| 4-(4-(2-(4-propylcyclohexyl)ethyl)cyclohexyl)-1,2,6-trifluorobenzene | 5% |
| 4-(4-(2-(4-pentylcyclohexyl)ethyl)cyclohexyl)-1,2,6-trifluorobenzene | 5% |
| 4-(2-(4'-propylbicyclohexyl)ethyl)-1,2,6-tri-fluorobenzene | 5% |
| 4-(2-(4'-pentylbicyclohexyl)ethyl)-1,2,6-tri-fluorobenzene | 5% |
| 4-(4-heptylcyclohexyl)-1,2,6-trifluorobenzene | 9% |
| 4'-(2)-4-propylcyclohexyl)ethyl)-3,4,5-trifluoro-biphenyl | 8% |
| 4'-(2)-4-pentylcyclohexyl)ethyl)-3,4,5-trifluoro-biphenyl | 8% |

Its values of physical properties were measured. The results were as follows:

Clearing point: 73.2° C.,

Δn: 0.0811, Δε: 6.0, viscosity η at 20° C.: 20.0 mPas, and threshold voltage in a cell thickness of 8.7 μm: 1.99 volt.

Effect of the Invention

The compound of the present invention has the following characteristics:

(1) a large Δn, (2) a low viscosity, (3) a superior chemical stability and a high voltage-holding ratio, (4) a very high compatibility with other liquid crystal-line compounds, while having a high clearing point, so that when a liquid crystal composition is prepared therefrom, reduction of nematic liquid crystal phase is not caused, and it can be mixed in a high proportion, and (5) a very high Δε.

Thus, when the compound of the present invention is used, it is possible to obtain a liquid crystal composition having a large Δn, and a low viscosity (effective for improving the response speed to the change in the electric field), a high voltage-holding ratio, and exhibiting a nematic liquid crystal phase in a broad temperature range. Further, since the compound of the present invention has a high Δε, it is possible to reduce the driving voltage, and when it is used, it is possible to provide a liquid crystal composition preferably used particularly for TFT.

What is claimed is:

1. A liquid crystalline compound expressed by the formula (I)

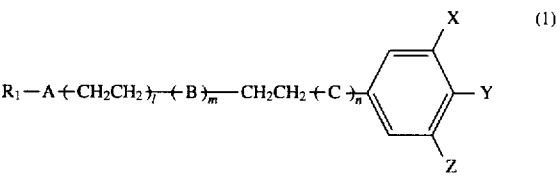

wherein $R_1$ represents an alkyl group of 1 to 12 carbon atoms and one or two not adjacent $CH_2$ groups excluding the terminal in the alkyl group may be replaced by oxygen atom, —CO— group, —OCO— group, —COO— group or —CH=CH— group; X and Z each represent H, F or Cl atom; Y represents a trifluoromethyl or difluormethyloxy group; one of A, B and C represents cyclohexene ring and the others thereof can be chosen from among covalent bond or cyclohexane ring and benzene rings and these rings may be substituted by F atom or Cl atom; and l, m and n each are 0 or 1 independently of each other, but when m=0, l=0.

2. A liquid crystalline compound according to claim 1, wherein $R_1$ represents an alkyl group or an alkyloxy group of 1 to 12 carbon atoms.

3. A liquid crystalline compound according to claim 1, wherein Y represents trifluoromethyl group.

4. A liquid crystalline compound according to claim 1, wherein Y represents difluoromethyloxy group.

5. A liquid crystal composition comprising two or more components at least one of which is a liquid crystalline compound set forth in one of claims 1 to 3 or 5.

6. A liquid crystal composition comprising as a first component, at least one compound set forth in one of claims 1 to 3 or 4 and as a second component, at least one compound chosen from among those of the following formulas (2), (3) and (4):

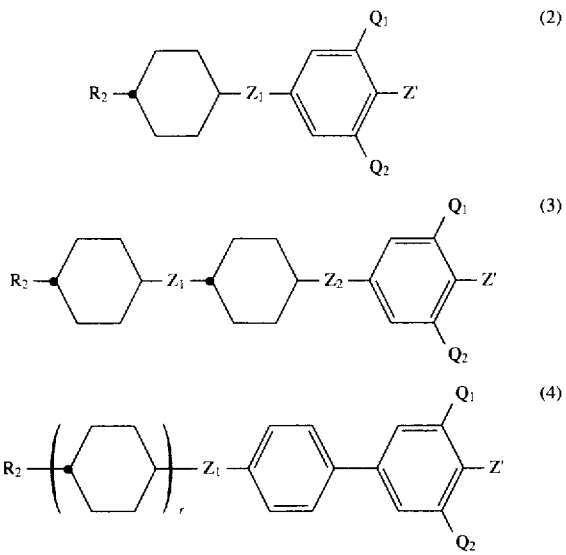

wherein $R_2$ represents an alkyl group of 1 to 10 carbon atoms; $Z'$ represents F or Cl; $Q_1$ and $Q_2$ each represent H or F independently of each other; r represents 1 or 2; and $Z_1$ and $Z_2$ each represent —$CH_2CH_2$— or covalent bond independently of each other.

7. A liquid crystal composition comprising as a first component, at least one compound set forth in one of claims 1 to 3 or 4, and as a second component, at least one compound chosen from among those of the following formulas (5), (6), (7), (8) and (9):

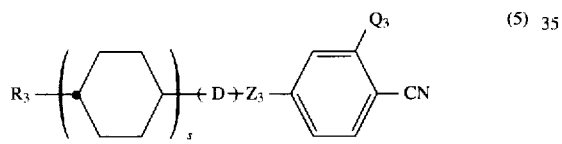

wherein $R_3$ represents an alkyl group of 1 to 10 carbon atoms or an alkenyl group of 2 to 10 carbon atoms and optional methylene group (—$CH_2$—) excluding the terminal in these groups may be replaced by oxygen atom (—O—), but two or more methylene groups should not be continuedly replaced by oxygen atom; $Z_3$ represents —$CH_2CH_2$—, —COO— or covalent bond; $Q_3$ represents H or F; D represents cyclohexane ring, benzene ring or 1,3-dioxane ring; and s represents 0 or 1,

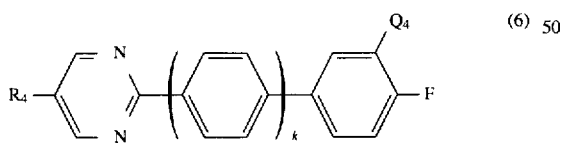

wherein $R_4$ represents an alkyl group of 1 to 10 carbon atoms, and optional methylene group (—$CH_2$—) excluding the terminal in the group may be replaced by oxygen atom (—O—), but two or more methylene groups should not be continuedly replaced by oxygen atom; $Q_4$ represents H or F; and k represents 0 or 1,

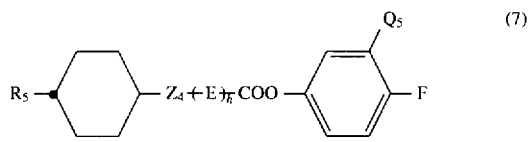

wherein $R_5$ represents an alkyl group of 1 to 10 carbon atoms, and optional methylene group (—$CH_2$—) excluding the terminal in the group may be replaced by oxygen atom (—O—), but two or more methylene groups should not be continuedly replaced by oxygen atom; E represents cyclohexane ring or benzene ring; $Q_5$ represents H or F; $Z_4$ represents —COO— or covalent bond; and h represents 0 or 1,

wherein $R_6$ and $R_7$ each represent an alkyl group, an alkyloxy group or an alkyloxymethyl group of 1 to 10 carbon atoms, independently of each other, and optional methylene groups (—$CH_2$—) excluding the terminal in these groups may be replaced by oxygen atom, but two or more methylene groups should not be continuedly replaced by two or more oxygen atoms; L represents cyclohexane ring, pyrimidine ring or benzene ring; G represents cyclohexane ring or benzene ring; and $Z_5$ represents —C≡C—, —COO—, —$CH_2CH_2$— or covalent bond,

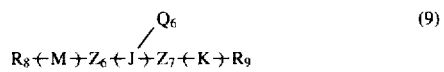

wherein $R_8$ represents an alkyl group or an alkyloxy group of 1 to 10 carbon atoms; $R_9$ represents an alkyl group, an alkyloxy group or an alkyloxymethyl group of 1 to 10 carbon atoms, and optional methylene group (—$CH_2$—) excluding the terminal in these groups may be replaced by oxygen atom (—O—), but two or more methylene groups should not be continuedly replaced by oxygen atom; M represents cyclohexane ring or pyrimidine ring; J and K each represent cyclohexane ring or benzene ring independently of each other; $Z_6$ represents —COO—, —$CH_2CH_2$— or covalent bond; $Z_7$ represents —C≡C—, —COO— or covalent bond; and $Q_6$ represents H or F.

8. A liquid crystal display element composed using a liquid crystal composition comprising two or more components, at least one of which contains at least one liquid crystalline compound recited in one of claims 1 to 3 or 4.

9. A liquid crystal display element composed using a liquid crystal composition recited in claim 6.

10. A liquid crystal display element composed using a liquid crystal composition recited in claim 7.

* * * * *

UNITED STATES PATENT AND TRADEMARK OFFICE
CERTIFICATE OF CORRECTION

PATENT NO. : 5,534,187
DATED : July 9, 1996
INVENTOR(S) : Kazutoshi MIYAZAWA, Shuichi MATSUI, Yasuyuki GOTO, Etsuo NAKAGAWA, and Shinichi SAWADA It is certified that error appears in the above-indentified patent and that said Letters Patent is hereby corrected as shown below:

Column 67, line 39, change "m, n=1" to --m=1, n=0--.

Column 69, line 4, change "m, n=1" to --m=1, n=0--.

Column 89, in the second compound from the bottom (line 4 from the bottom, disregarding the line numbers between columns 89 and 90), change "(2)-" to --(2-(--;

and the first compound from the bottom (line 2 from the bottom, disregarding the line numbers between columns 89 and 90), change "(2)-" to --(2-(--.

Signed and Sealed this

Tenth Day of December, 1996

BRUCE LEHMAN

Attest:

Attesting Officer

Commissioner of Patents and Trademarks